(12) United States Patent
Hattori et al.

(10) Patent No.: US 10,729,395 B2
(45) Date of Patent: Aug. 4, 2020

(54) IMAGE PROCESSING DEVICE AND METHOD FOR OPERATING IMAGE PROCESSING DEVICE

(71) Applicant: FUJIFILM Corporation, Tokyo (JP)

(72) Inventors: Masato Hattori, Kanagawa (JP); Ryo Imamura, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 168 days.

(21) Appl. No.: 16/059,725

(22) Filed: Aug. 9, 2018

(65) Prior Publication Data

US 2019/0046135 A1   Feb. 14, 2019

(30) Foreign Application Priority Data

Aug. 10, 2017  (JP) .................................. 2017-156066

(51) Int. Cl.
| | | |
|---|---|---|
| A61B 6/00 | (2006.01) | |
| H04N 5/232 | (2006.01) | |
| G06K 9/32 | (2006.01) | |
| G06K 9/20 | (2006.01) | |
| G06K 9/62 | (2006.01) | |
| H04N 5/32 | (2006.01) | |

(52) U.S. Cl.
CPC .......... *A61B 6/4233* (2013.01); *A61B 6/4283* (2013.01); *A61B 6/469* (2013.01); *A61B 6/488* (2013.01); *A61B 6/5217* (2013.01); *A61B 6/545* (2013.01); *A61B 6/588* (2013.01); *A61B 6/589* (2013.01); *G06K 9/2018* (2013.01); *G06K 9/3233* (2013.01); *G06K 9/6289* (2013.01); *H04N 5/23229* (2013.01); *H04N 5/32* (2013.01)

(58) Field of Classification Search
CPC ..... A61B 6/4233; A61B 6/4283; A61B 6/588; A61B 6/589; A61B 6/545; A61B 6/488; A61B 6/5217; A61B 6/469; A61B 6/5223; H04N 5/32; H04N 5/23229; G06K 9/6289; G06K 9/2018; G06K 9/3233
USPC ....................................................... 382/132
See application file for complete search history.

(56) References Cited

U.S. PATENT DOCUMENTS

| | | | |
|---|---|---|---|
| 5,539,798 A * | 7/1996 | Asahina ................. | A61B 6/022 348/E5.086 |
| 2017/0135667 A1* | 5/2017 | Becker ................. | A61B 6/4411 |
| 2019/0046134 A1* | 2/2019 | Imamura .............. | A61B 6/4283 |
| 2019/0320995 A1* | 10/2019 | Amiri .................. | A61B 6/4405 |

FOREIGN PATENT DOCUMENTS

JP          2015-100592 A       6/2015

* cited by examiner

*Primary Examiner* — Juan A Torres
(74) *Attorney, Agent, or Firm* — Birch, Stewart, Kolasch & Birch, LLP

(57) ABSTRACT

A detection unit of a CPU of a console detects the position of an electronic cassette and the position of an irradiation field on the basis of a camera image output from a camera that is attached to an X-ray source and captures an image of at least the electronic cassette. The image processing unit performs image processing for an X-ray image detected by the electronic cassette on the basis of information of the position of the electronic cassette and information of the position of the irradiation field.

9 Claims, 15 Drawing Sheets

| IMAGE ID | IF0001 |
| --- | --- |
| IMAGING DATE AND TIME | 7/10/2017  11:05 |
| SUBJECT ID | H0500 |
| NAME | ○○○○ |
| SEX | MALE |
| DATE OF BIRTH | 09/25/1985 |
| AGE | 28 |
| HEIGHT | 183 |
| WEIGHT | 78 |
| ORDER ID | OD0001 |
| IMAGING MENU | HAND/SEATED POSITION/FRONT |
| TUBE VOLTAGE | 100 |
| TUBE CURRENT | 200 |
| IRRADIATION TIME | 20 |

FIG. 16
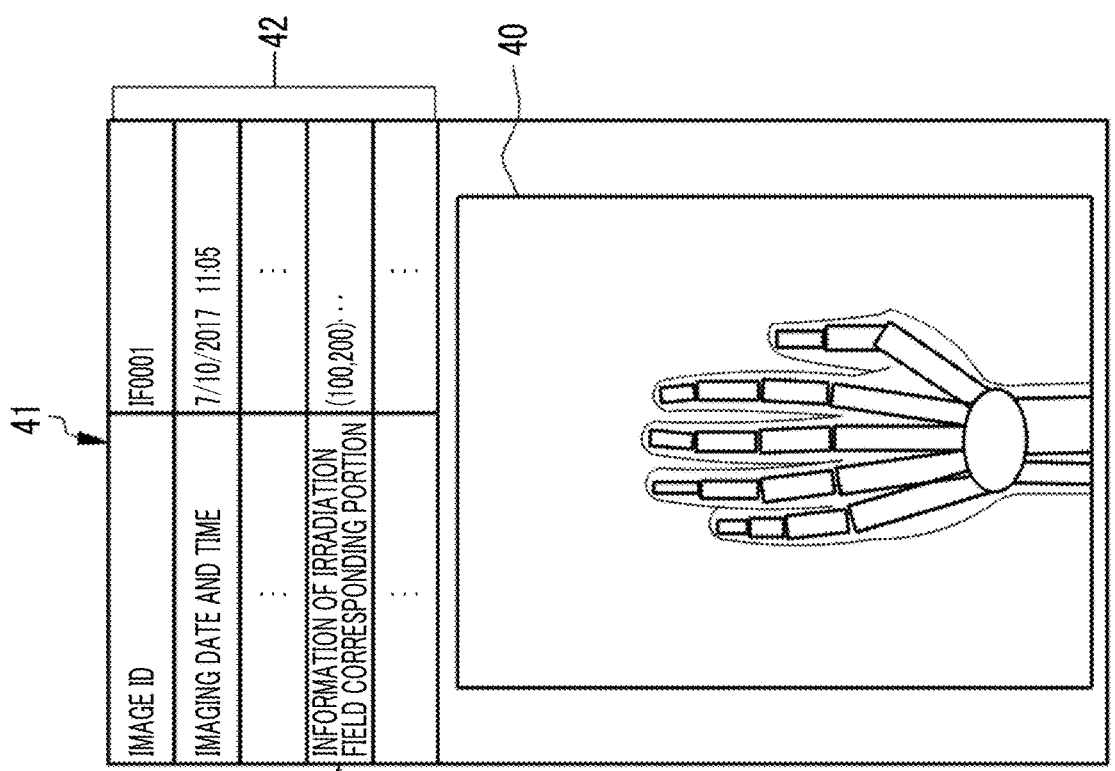
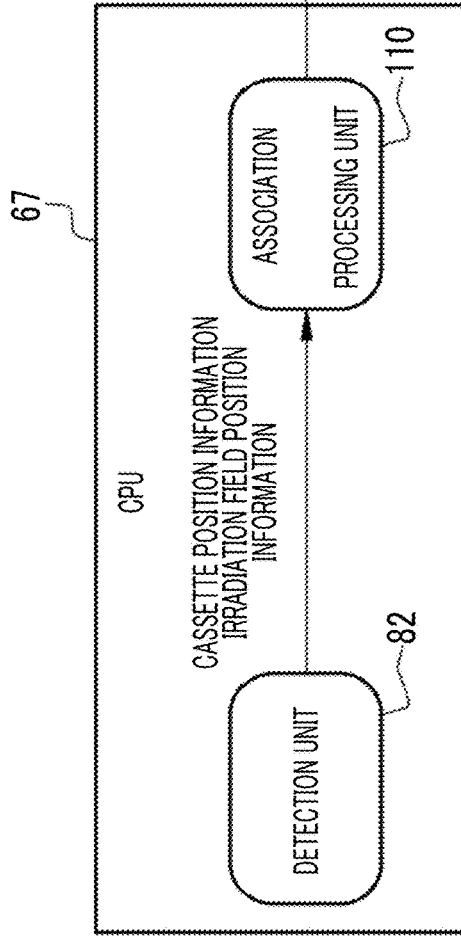

IMAGE PROCESSING DEVICE AND METHOD FOR OPERATING IMAGE PROCESSING DEVICE

CROSS-REFERENCE TO RELATED APPLICATION

This application claims priority under 35 USC 119 from Japanese Patent Application No. 2017-156066, filed 10 Aug. 2017, the disclosure of which is incorporated by reference herein.

BACKGROUND OF THE INVENTION

1. Field of the Invention

The present invention relates to an image processing device and a method for operating the image processing device.

2. Description of the Related Art

In a medical field, a diagnosis is made on the basis of a radiographic image detected by a radiographic image detection device. The radiographic image detection device includes a sensor panel. The sensor panel is provided with an imaging region. A plurality of pixels are two-dimensionally arranged in the imaging region. The pixel is sensitive to radiation which has been emitted from a radiation source and then transmitted through a subject (patient) and accumulates charge. The radiographic image detection device converts the charge accumulated in the pixel into a digital signal and outputs the digital signal as a radiographic image.

The radiographic image detection devices are classified into a fixed type that is fixed to an imaging stand installed in an imaging room and a portable type in which, for example, a sensor panel is accommodated in a portable housing. The portable radiographic image detection device is referred to as an electronic cassette. The electronic cassettes are classified into a wired type that is supplied with power from a commercial power supply through a cable and a wireless type that is supplied with power from a battery provided in a housing.

The electronic cassette is carried out of the imaging room and is then used since it has high mobility. For example, the electronic cassette is used for visit imaging in which an operator visits a hospital room in which a patient who is not able to move to the imaging room is present and takes a radiographic image. In addition, the electronic cassette is used in places other than medical facilities in order to capture a radiographic image of an aged person who gets medical treatment at home or a patient who is in an emergency situation due to an accident or a disaster. Hereinafter, imaging without using an imaging stand is referred to as free imaging.

However, the radiation source is provided with an irradiation field limiter (which is also referred to as a collimator). The irradiation field limiter has an irradiation opening for setting an irradiation field. Here, the irradiation field is a region that is irradiated with radiation. An operator, such as a radiology technician, changes the size of the irradiation opening of the irradiation field limiter to set the irradiation field corresponding to an imaging order from a person who requests imaging such as a doctor.

In some cases, the entire imaging region of the sensor panel does not become the irradiation field depending on the content of the imaging order and a region (hereinafter, referred to as a non-irradiation field) that is not irradiated with radiation is generated in the imaging region. In this case, a portion of the radiographic image (hereinafter, referred to as a non-irradiation field corresponding portion) corresponding to the non-irradiation field is displayed in white and the contrast between the non-irradiation field corresponding portion and a portion (hereinafter, an irradiation field corresponding portion) which is displayed in black and corresponds to the irradiation field is too high, which hinders observation.

In the related art, for example, as disclosed in JP2015-100592A, in a case in which a radiographic image is displayed, the position of the irradiation field is detected and a blackening process which colors a portion other than the irradiation field corresponding portion corresponding to the detected irradiation field, that is, the non-irradiation field corresponding portion black or a trimming process which trims the non-irradiation field corresponding portion is performed for the radiographic image.

In JP2015-100592A, the radiographic image is analyzed to detect the position of the irradiation field. For example, a portion in which pixel values (density) change rapidly in the radiographic image is extracted as the boundary (edge) between the irradiation field and the non-irradiation field and a rectangular region formed at the extracted boundary is detected as the irradiation field. Alternatively, a dynamic contour extraction algorithm which is typified by a Snake method is applied to the radiographic image to extract the contour of the irradiation field and the irradiation field is detected.

SUMMARY OF THE INVENTION

However, the irradiation field is not limited to the rectangular shape and is set in various shapes. In the radiographic image, the pixel values vary depending on radiation emission conditions. In addition, the radiation has the properties of being scattered or diffracted. Therefore, in some cases, the contour of the irradiation field in the radiographic image is unclear. As a result, in the method which analyzes the radiographic image to detect the position of the irradiation field as in JP2015-100592A, the reliability of the detected position of the irradiation field is not very high.

An object of the invention is to provide an image processing device that can detect the exact position of an irradiation field and perform appropriate image processing for a radiographic image, and a method for operating the image processing device.

In order to achieve the object, there is provided an image processing device comprising: a radiographic image acquisition unit that acquires a radiographic image which is based on radiation that has been emitted from a radiation source and transmitted through a subject and is detected by an electronic cassette; a camera image acquisition unit that acquires a camera image output from a camera which is attached to the radiation source and captures an image of at least the electronic cassette; a detection unit that detects a position of the electronic cassette and a position of an irradiation field which is a region irradiated with the radiation on the basis of the camera image; and an image processing unit that performs image processing for the radiographic image on the basis of information of the position of the electronic cassette and information of the position of the irradiation field.

Preferably, the radiation source includes an irradiation field display light source that emits irradiation field display light indicating the irradiation field and the detection unit detects the position of the irradiation field on the basis of the irradiation field display light included in the camera image.

Preferably, the electronic cassette is provided with an imaging region for detecting the radiographic image. Preferably, the image processing device further comprises: a first acquisition unit that acquires a reference size LIM0 of the irradiation field in the camera image at a predetermined reference distance SID0 from a focal position of a radiation tube of the radiation source as an end point; and a second acquisition unit that acquires a distance SID1 between the focal position and the imaging region during radiography. Preferably, the detection unit calculates a size LIM1 of the irradiation field in the camera image during radiography from the reference size LIM0 acquired by the first acquisition unit, the reference distance SID0, and the distance SID1 acquired by the second acquisition unit.

Preferably, the radiation source includes an irradiation field limiter having an irradiation opening for setting the irradiation field and the first acquisition unit acquires a size of the irradiation opening during radiography and acquires the reference size LIM0 corresponding to the acquired size of the irradiation opening.

Preferably, the image processing unit includes a first image processing unit that performs first image processing as the image processing for an irradiation field corresponding portion which is a portion of the radiographic image corresponding to the irradiation field or/and a second image processing unit that performs second image processing as the image processing for a non-irradiation field corresponding portion which is a portion of the radiographic image corresponding to a non-irradiation field that is a region which is other than the irradiation field and is not irradiated with the radiation.

Preferably, the first image processing unit performs, as the first image processing, multi-frequency processing and a dynamic range compression process for the irradiation field corresponding portion. Preferably, the second image processing unit performs, as the second image processing, a blackening process that colors the non-irradiation field corresponding portion black or a trimming process that trims the non-irradiation field corresponding portion and leaves only the irradiation field corresponding portion.

Preferably, the image processing device further comprises an association processing unit that associates information of the irradiation field corresponding portion or the non-irradiation field corresponding portion as accessory information of the radiographic image with the radiographic image.

According to another aspect of the invention, there is provided a method for operating an image processing device. The method comprises: a radiographic image acquisition step of acquiring a radiographic image which is based on radiation that has been emitted from a radiation source and transmitted through a subject and is detected by an electronic cassette; a camera image acquisition step of acquiring a camera image output from a camera which is attached to the radiation source and captures an image of at least the electronic cassette; a detection step of detecting a position of the electronic cassette and a position of an irradiation field which is a region irradiated with the radiation on the basis of the camera image; and an image processing step of performing image processing for the radiographic image on the basis of information of the position of the electronic cassette and information of the position of the irradiation field.

According to the invention, the position of an electronic cassette and the position of an irradiation field which is a region irradiated with radiation are detected on the basis of a camera image output from a camera which is attached to a radiation source and captures an image of at least the electronic cassette and image processing is performed for the radiographic image on the basis of information of the detected position of the electronic cassette and information of the detected position of the irradiation field. Therefore, it is possible to provide an image processing device that can detect the exact position of the irradiation field and perform appropriate image processing for the radiographic image and a method for operating the image processing device.

BRIEF DESCRIPTION OF THE DRAWINGS

FIG. 16 is a block diagram illustrating a CPU of a console according to a third embodiment.

DESCRIPTION OF THE PREFERRED EMBODIMENTS

First Embodiment

Figure 1:
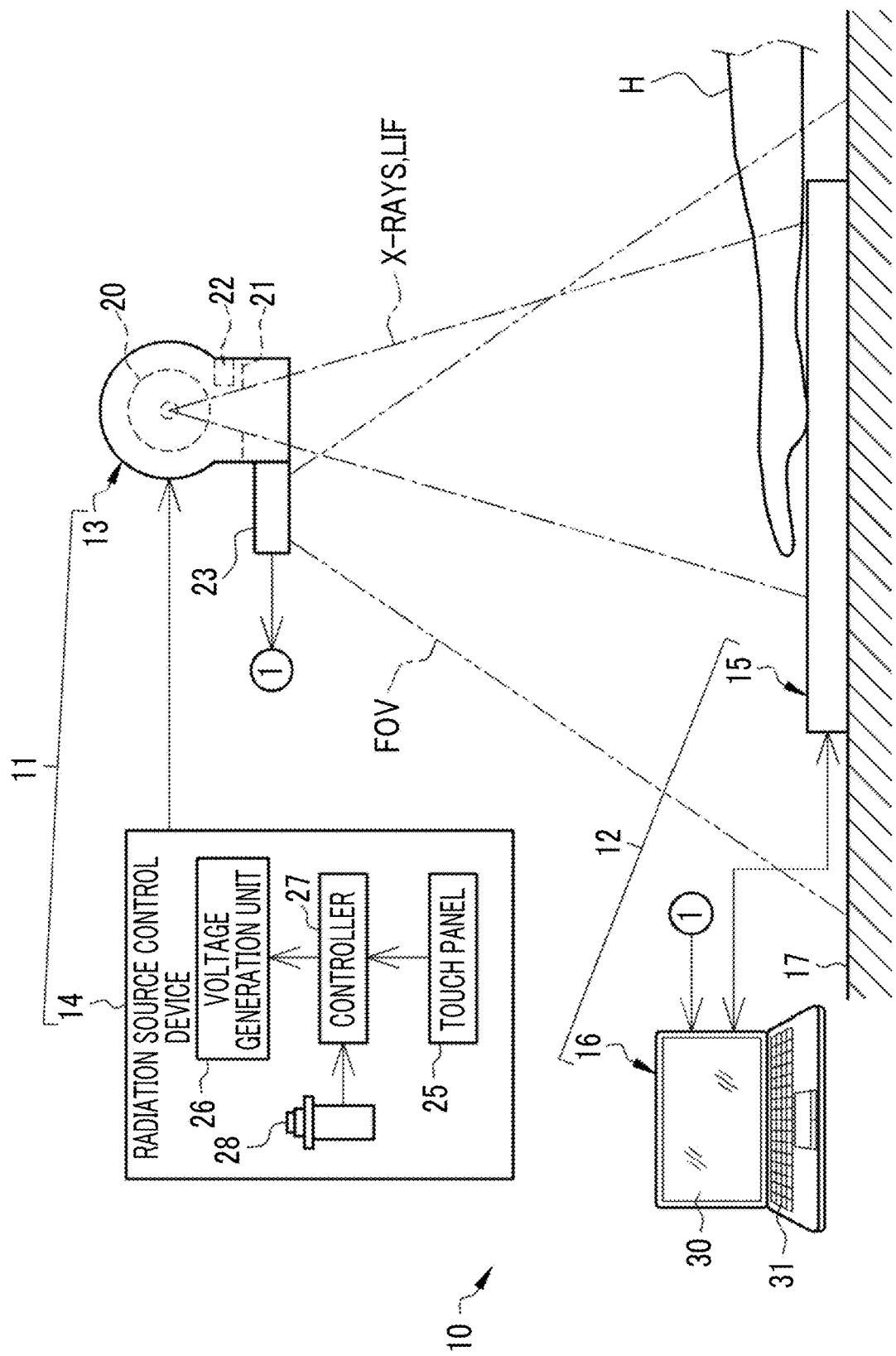
FIG. 1 is a diagram illustrating an X-ray imaging system.

In FIG. 1, an X-ray imaging system 10 that uses X-rays as radiation includes an X-ray generation apparatus 11 and an X-ray imaging apparatus 12. The X-ray generation apparatus 11 includes an X-ray source 13 corresponding to a radiation source and a radiation source control device 14. The X-ray imaging apparatus 12 includes an electronic cassette 15 and a console 16 corresponding to an image processing device.

FIG. 1 illustrates an aspect in which, in an imaging room in which the X-ray imaging system 10 is installed, the electronic cassette 15 is placed on a table 17 that faces the X-ray source 13, an imaging part (in this example, a hand) of a subject H is placed on the electronic cassette 15, and X-ray imaging is performed. That is, the X-ray imaging illustrated in FIG. 1 is free imaging without using an imaging stand.

The X-ray source 13 includes an X-ray tube 20 that generates X-rays, an irradiation field limiter 21 that limits an irradiation field IF (see FIG. 3) which is a region irradiated with X-rays, and an irradiation field display light source 22 that emits irradiation field display light LIF (also see, for example, FIG. 3) indicating the irradiation field IF.

The X-ray tube 20 includes a filament that emits thermal electrons and a target that collides with the thermal electrons emitted from the filament and emits X-rays. The irradiation field limiter 21 has, for example, a structure in which four lead plates that shield X-rays are provided on each side of a rectangle and a rectangular irradiation opening which transmits X-rays is provided at the center. In this case, the irradiation field limiter 21 moves the positions of the lead plates to change the size of the irradiation opening, thereby setting the irradiation field IF. The irradiation field display light source 22 emits the irradiation field display light LIF through the irradiation opening of the irradiation field limiter 21. Therefore, the irradiation field display light LIF literally has the same shape and size as the irradiation field IF. The irradiation field display light source 22 emits the irradiation field display light LIF of a special color (for example, yellow) such that an operator can visually recognize the irradiation field display light LIF in the imaging room in which the light is dimmed.

An optical camera 23 is attached to the X-ray source 13. After the operator relatively positions the X-ray source 13, the electronic cassette 15, and the subject H for X-ray imaging, the camera 23 puts the electronic cassette 15 and the subject H into a field of view (hereinafter, referred to as an FOV). The camera 23 captures a camera image 63 (see FIG. 6) which is an optical image including the electronic cassette 15 and the subject H. The camera image 63 is, for example, a color image and is a still image.

Here, a case in which "a camera is attached to a radiation source" described in the claims includes a case in which a camera is directly attached to a peripheral portion of the X-ray source 13 as illustrated in FIG. 1 and a case in which a camera is provided in the X-ray source 13 like the irradiation field display light source 22. In addition, the case in which "a camera is attached to a radiation source" described in the claims includes a case in which an objective lens is provided in the peripheral portion of the X-ray source 13 and an imaging element is provided in a portion (for example, an arm that hangs the X-ray source 13 from the ceiling) other than the X-ray source 13.

The camera 23 includes a wireless communication unit and a battery and is wirelessly operated. The camera 23 wirelessly receives an imaging command signal from the console 16 and captures the camera image 63 in response to the imaging command signal. The camera 23 wirelessly transmits the captured camera image 63 to the console 16.

The radiation source control device 14 includes a touch panel 25, a voltage generation unit 26, a controller 27, and an irradiation switch 28. The touch panel 25 is operated in a case in which X-ray emission conditions including a tube voltage and a tube current applied to the X-ray tube 20 and an X-ray emission time and the size of the irradiation opening of the irradiation field limiter 21 are set. Here, the tube current is a parameter for determining the flow rate of thermal electrons emitted from the filament of the X-ray tube 20 to the target.

The voltage generation unit 26 generates the tube voltage to be applied to the X-ray tube 20. The controller 27 controls the operation of the voltage generation unit 26 to control the tube voltage, the tube current, and the X-ray emission time. The controller 27 includes a timer that starts to measure time in a case in which the X-ray tube 20 generates X-rays and stops the operation of the X-ray tube 20 in a case in which the time measured by the timer reaches the irradiation time set in the irradiation conditions. The controller 27 operates the irradiation field limiter 21 such that the size of the irradiation opening is equal to the size set through the touch panel 25.

The irradiation switch 28 is operated by the operator in a case in which the emission of X-rays starts. The irradiation switch 28 is pressed in two stages. In a case in which the irradiation switch 28 is pressed to the first stage (halfway), the controller 27 directs the X-ray tube 20 to start a preparation operation before generating X-rays. In a case in which the irradiation switch 28 is pressed to the second stage (fully), the controller 27 directs the X-ray tube 20 to generate X-rays. In this way, X-rays are emitted to the hand which is an imaging part of the subject H.

The electronic cassette 15 detects an X-ray image 40 (see FIG. 2) based on the X-rays which have been emitted from the X-ray source 13 and then transmitted through the subject H. Similarly to the camera 23, the electronic cassette 15 includes a wireless communication unit and a battery and is wirelessly operated. The electronic cassette 15 wirelessly transmits the X-ray image 40 to the console 16.

The console 16 is implemented by installing, for example, a control program, such as an operating system, or various application programs in a computer such as a notebook personal computer. The console 16 includes a display 30 and an input device 31, such as a touch pad or a keyboard. The console 16 displays various operation screens with an operation function through a graphical user interface (GUI) on the display 30 and receives various operation commands input from the input device 31 by the operator through various operation screens.

The various operation commands input through the input device 31 include, for example, a condition setting command including an imaging menu and irradiation conditions corresponding to the imaging menu. The imaging menu defines, for example, an imaging procedure having a set of an imaging part, a posture, and a direction. Examples of the imaging part include the head, the cervical vertebra, the chest, the abdomen, a finger, an elbow, an arm, and a knee in addition to the hand illustrated in FIG. 1. The posture is the posture of the subject H, such as an upright position, a decubitus position, and a seated position, and the direction is the direction of the subject H with respect to the X-ray source 13, such as the front, the side, and the rear. The condition setting command is a command to set an imaging menu and irradiation conditions corresponding to an imaging order and is input by the operator. For example, the imaging order is issued from a person who requests imaging, such as a doctor in a diagnosis and treatment department, to the operator in order to command X-ray imaging. In a case in which the condition setting command is input through the input device 31, the console 16 wirelessly transmits the condition setting signal including the set imaging menu and irradiation conditions to the electronic cassette 15.

The various operation commands include a command to capture the camera image 63. In a case in which the command to capture the camera image 63 is input through the input device 31, the console 16 wirelessly transmits the imaging command signal to the camera 23.

Figure 2:
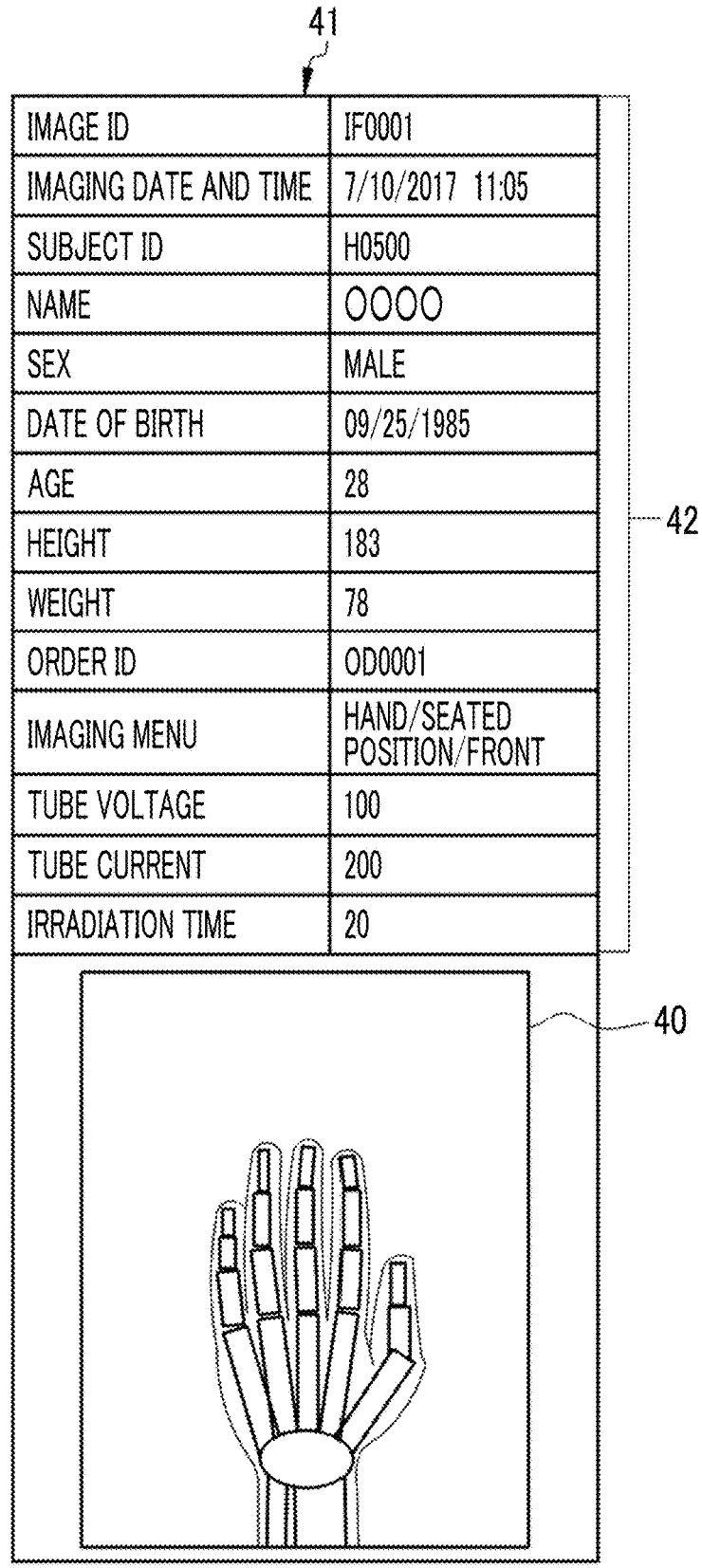
FIG. 2 is a diagram illustrating an image file.

For example, the console 16 converts the X-ray image 40 from the electronic cassette 15 into an image file 41 in the format based on a Digital Imaging and Communication in Medicine (DICOM) standard illustrated in FIG. 2. Then, the console 16 transmits the image file 41 to a picture archiving and communication system (PACS) (not illustrated).

In the image file 41, the X-ray image 40 and accessory information 42 are associated with each other by one image ID. The accessory information 42 includes, for example, subject information including the name and sex of the subject H, an order ID, an imaging menu, and irradiation conditions. The order ID is a symbol or a number for identifying the imaging order.

Figure 3:
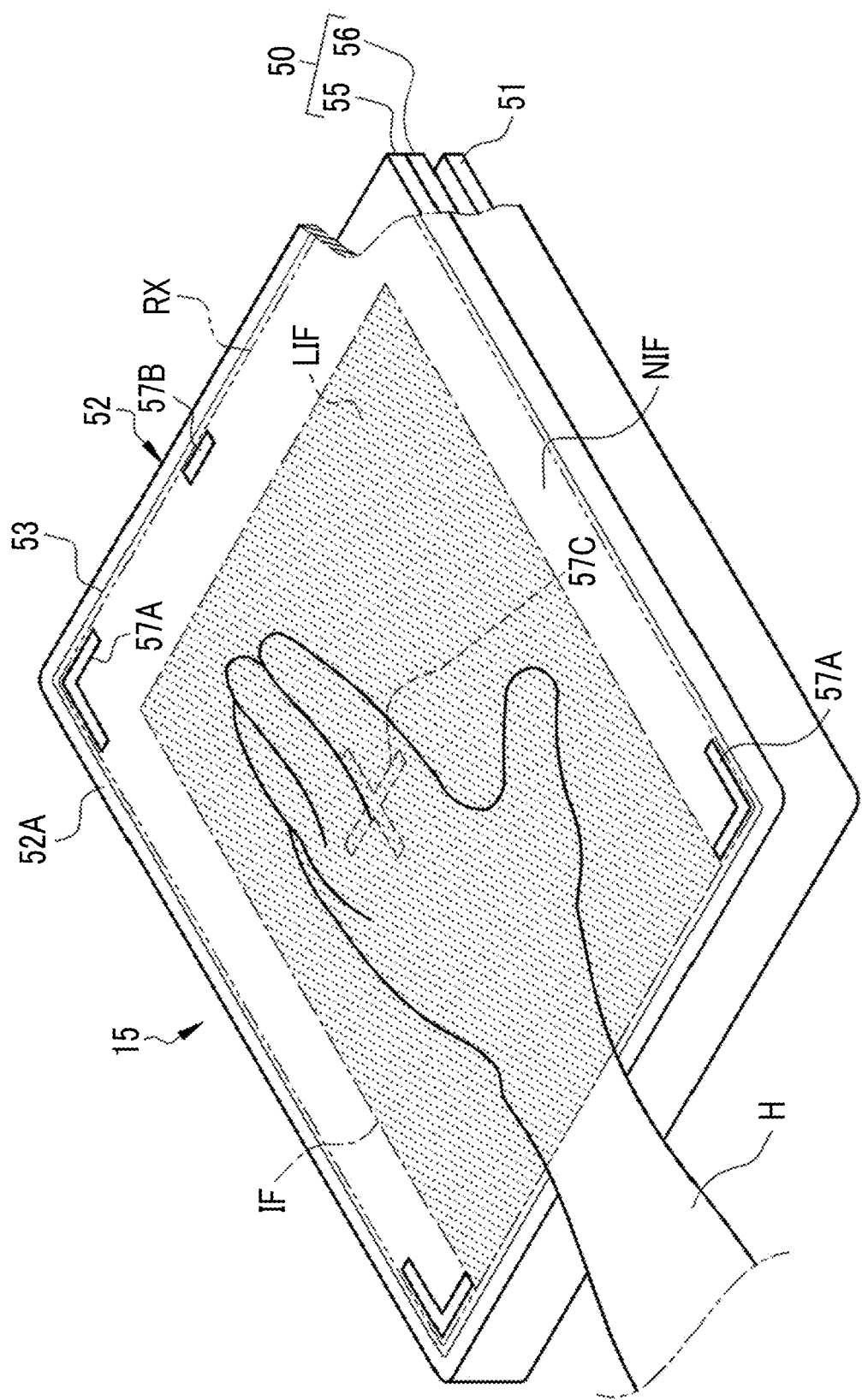
FIG. 3 is a perspective view illustrating the outward appearance of an electronic cassette.

In FIG. 3, the electronic cassette 15 includes a sensor panel 50, a circuit unit 51, and a portable housing 52 having a rectangular parallelepiped shape capable of accommodating the sensor panel 50 and the circuit unit 51. The housing 52 has a size based on International Organization for Standardization (ISO) 4090:2001 which is substantially equal to the size of a film cassette, an imaging plate (IP) cassette, or a computed radiography (CR) cassette.

A rectangular opening is formed in the front surface 52A of the housing 52 and a transmission plate 53 that transmits X-rays is attached to the opening. The electronic cassette 15 is positioned such that the front surface 52A faces the X-ray source 13 and the front surface 52A is irradiated with X-rays. In addition, the housing 52 is provided with a switch for turning on or off a main power supply and an indicator indicating the operating state of the electronic cassette 15 such as the remaining operating time of the battery or the completion state of preparation for imaging.

The sensor panel 50 includes a scintillator 55 and an optical detection substrate 56. The scintillator 55 and the optical detection substrate 56 are stacked in the order of the scintillator 55 and the optical detection substrate 56 as viewed from the front surface 52A. The scintillator 55 has a phosphor, such as CsI:Tl (thallium-activated cesium iodide) or GOS ($Gd_2O_2S$:Tb, terbium-activated gadolinium oxysulfide), converts the X-rays incident through the transmission plate 53 into visible light, and emits the visible light. In addition, a sensor panel may be used in which the optical detection substrate 56 and the scintillator 55 are stacked in this order as viewed from the front surface 52A irradiated with the X-rays. Furthermore, a direct-conversion-type sensor panel may be used which directly converts the X-rays into signal charge using a photoconductive film such as an amorphous selenium film.

The optical detection substrate 56 detects the visible light emitted from the scintillator 55 and converts the visible light into charge. The circuit unit 51 controls the driving of the optical detection substrate 56 and generates the X-ray image 40 on the basis of the charge output from the optical detection substrate 56.

An imaging region RX is provided in the optical detection substrate 56. The imaging region RX has a size that is substantially equal to the size of the transmission plate 53 and includes a plurality of pixels which are arranged in a two-dimensional matrix of N rows and M columns. The pixel is sensitive to the visible light from the scintillator 55 and accumulates charge. The circuit unit 51 converts the charge accumulated in the pixel into a digital signal to detect the X-ray image 40.

Here, N and M are integers that are equal to or greater than 2. For example, N and M are about 2000. In addition, the number of pixels in the matrix is not limited thereto. The array of the pixels may be a square array. Alternatively, the pixels may be inclined at 45° and may be arranged in zigzag.

L-shaped markers 57A are provided at four corners of the imaging region RX. In addition, a rod-shaped marker 57B is provided at the center of a short side of the imaging region RX. The side on which the rod-shaped marker 57B is provided is the upper side of the X-ray image 40. Furthermore, a cross-shaped marker 57C is provided at the center of the imaging region RX. The marker 57A is formed such that a long side is longer than a short side. The position and direction of the imaging region RX are known by the markers 57A to 57C.

FIG. 3 illustrates a state in which the hand of the subject H is placed on the electronic cassette 15 similarly to FIG. 1. FIG. 3 illustrates an aspect in which the irradiation field display light source 22 emits the irradiation field display light LIF (hatched with dashed lines) and the irradiation field IF represented by a one-dot chain line is irradiated with the irradiation field display light LIF.

In this example, the irradiation field IF has one side that is matched with one side of the imaging region RX and the wrist of the subject H and three sides that are parallel to the corresponding three sides of the imaging region RX. In addition, the irradiation field IF is set to a size that is slightly smaller than that of the imaging region RX. Therefore, a region other than the irradiation field IF which is not irradiated with X-rays, that is, a non-irradiation field NIF is generated in the imaging region RX.

Figure 4:
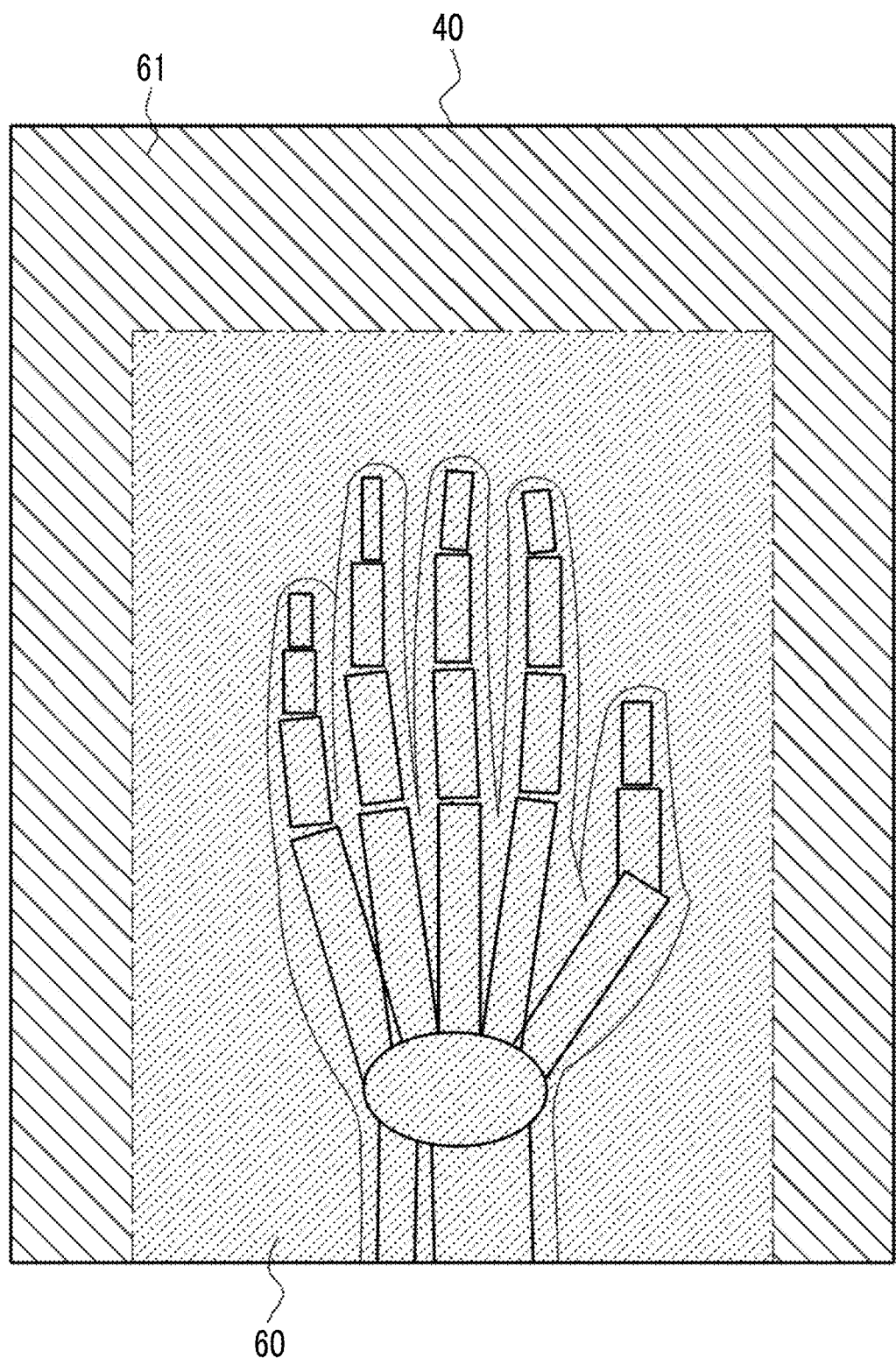
FIG. 4 is a diagram illustrating an X-ray image.

In this case, as illustrated in FIG. 4, the X-ray image 40 output from the electronic cassette 15 is divided into an irradiation field corresponding portion 60 (hatched with dashed lines) corresponding to the irradiation field IF and a non-irradiation field corresponding portion 61 (hatched with solid lines) corresponding to the non-irradiation field NIF. In the X-ray image 40, the display color of a portion that is irradiated with a larger amount of X-rays becomes closer to black. Therefore, since the irradiation field corresponding portion 60 is a portion that is irradiated with X-rays, the irradiation field corresponding portion 60 is displayed black. In contrast, since the non-irradiation field corresponding portion 61 is a portion that is not irradiated with X-ray's, the non-irradiation field corresponding portion 61 has the maximum brightness and is displayed white.

The electronic cassette 15 has a function of detecting the start of the emission of X-rays. For example, the irradiation start detection function is implemented by providing an irradiation start detection sensor in the imaging region RX of the optical detection substrate 56. Then, a dose signal corresponding to the amount of X-rays reaching the imaging region, which is output from the irradiation start detection sensor with a predetermined sampling period, is compared with a predetermined irradiation start detection threshold value. In a case in which the dose signal is greater than the irradiation start detection threshold value, it is determined that the emission of X-rays has been started. For example, some of the pixels take charge of the irradiation start detection sensor.

In addition, the electronic cassette 15 includes a timer that starts to measure time in a case in which the start of the emission of X-rays has been detected, similarly to the controller 27 of the radiation source control device 14. In a case in which the time measured by the timer reaches the irradiation time in the irradiation conditions set by the console 16, the electronic cassette 15 determines that the emission of X-rays has ended.

Figure 5:
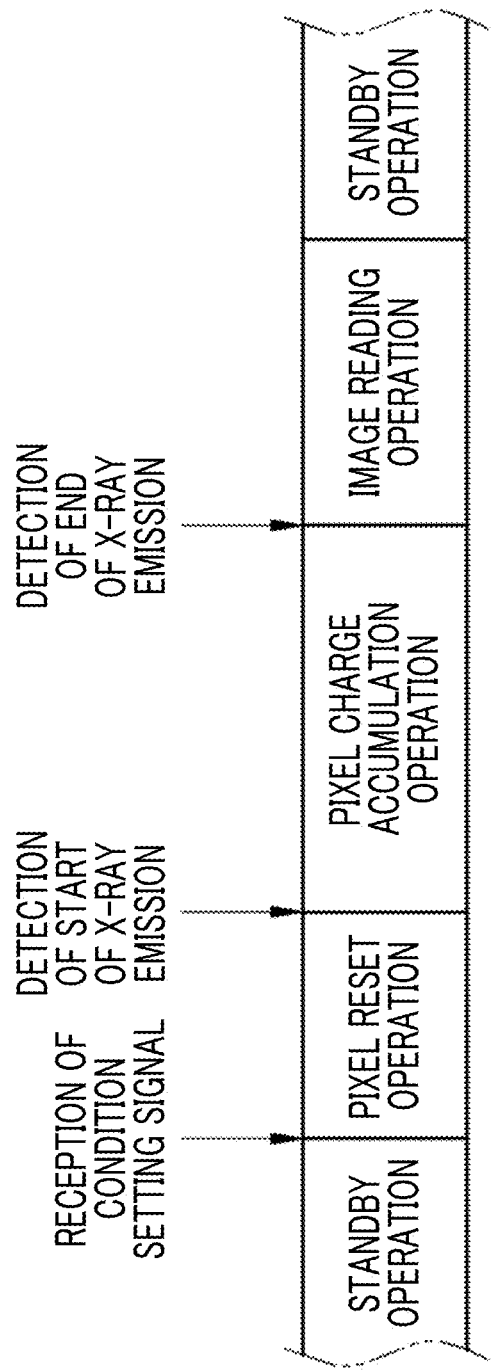
FIG. 5 is a diagram illustrating the flow of an operation performed by the electronic cassette.

As illustrated in FIG. 5, in a case in which the condition setting signal is received from the console 16, the electronic cassette 15 starts a pixel reset operation that reads dark charge from the pixel and resets (discards) the pixel. The electronic cassette 15 performs a standby operation before receiving the condition setting signal. The standby operation supplies power to only a minimum number of necessary units such as a wireless communication unit receiving the condition setting signal.

Then, in a case in which the start of the emission of X-rays has been detected by the irradiation start detection function, the electronic cassette 15 ends the pixel reset operation and starts a pixel charge accumulation operation that accumulates charge corresponding to the amount of X-rays reaching the pixel in the pixel. In this way, it is possible to synchronize the emission start time of X-rays from the X-ray source 13 with the start time of the pixel charge accumulation operation.

Then, in a case in which the end of the emission of X-rays has been detected by the timer, the electronic cassette 15 ends the pixel charge accumulation operation and starts an image reading operation for reading the X-ray image 40 to be used for diagnosis. In this way, one X-ray imaging operation for obtaining the X-ray image 40 corresponding to a single screen ends. After the image reading operation ends, the electronic cassette 15 returns to the standby operation again.

Figure 6:
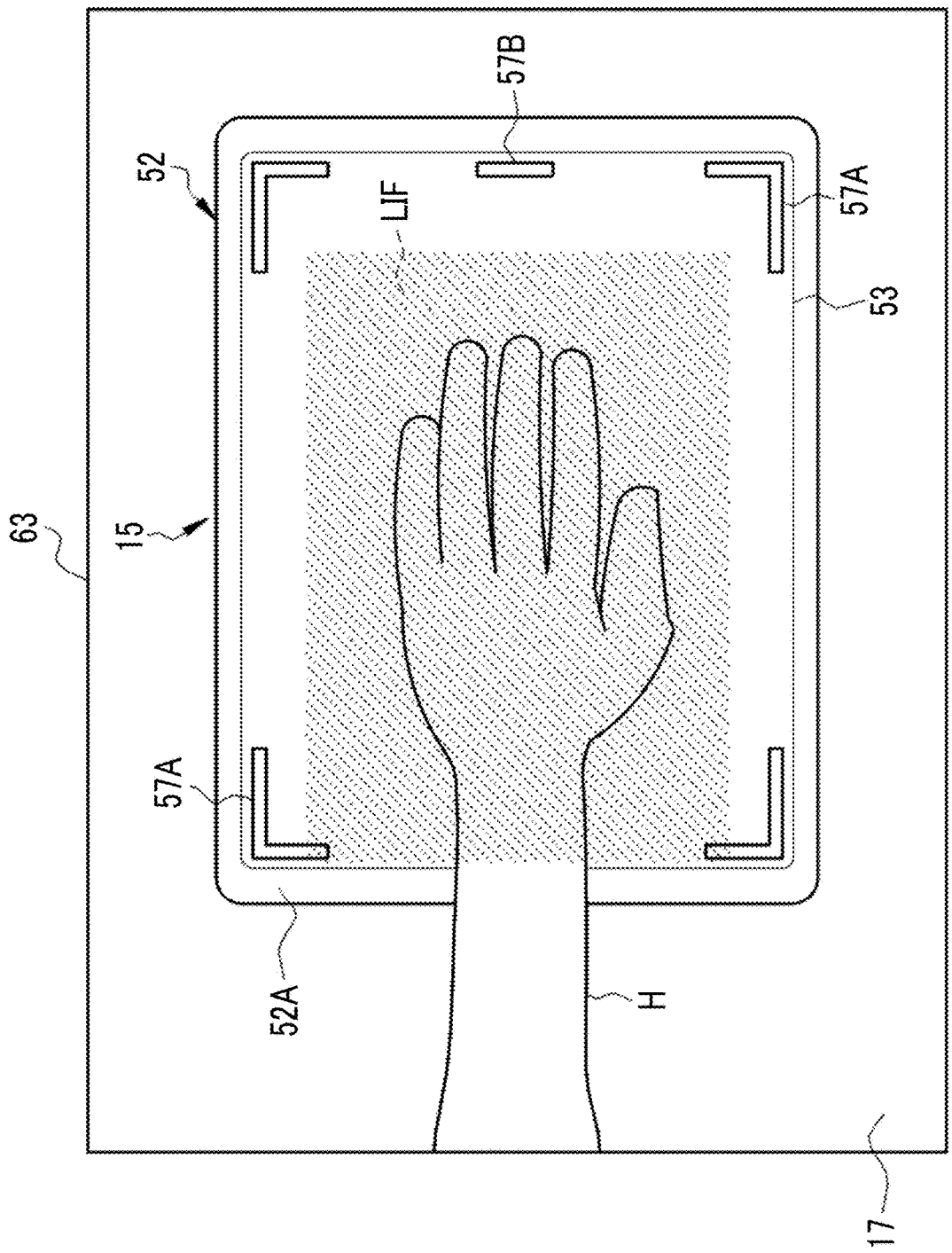
FIG. 6 is a diagram illustrating a camera image.

FIG. 6 illustrates the camera image 63 indicating an aspect of X-ray imaging illustrated in FIGS. 1 and 3. The camera image 63 includes the table 17, the electronic cassette 15 placed on the table 17, the hand of the subject H placed on the electronic cassette 15, and the irradiation field display light LIF emitted from the irradiation field display light source 22.

Since the camera 23 is attached to the X-ray source 13, the positional relationship between the X-ray source 13 and the camera 23 does not vary. Therefore, in the camera image 63, the irradiation field display light LIF and the center of the irradiation field IF are always located at the same positions.

Figure 7:
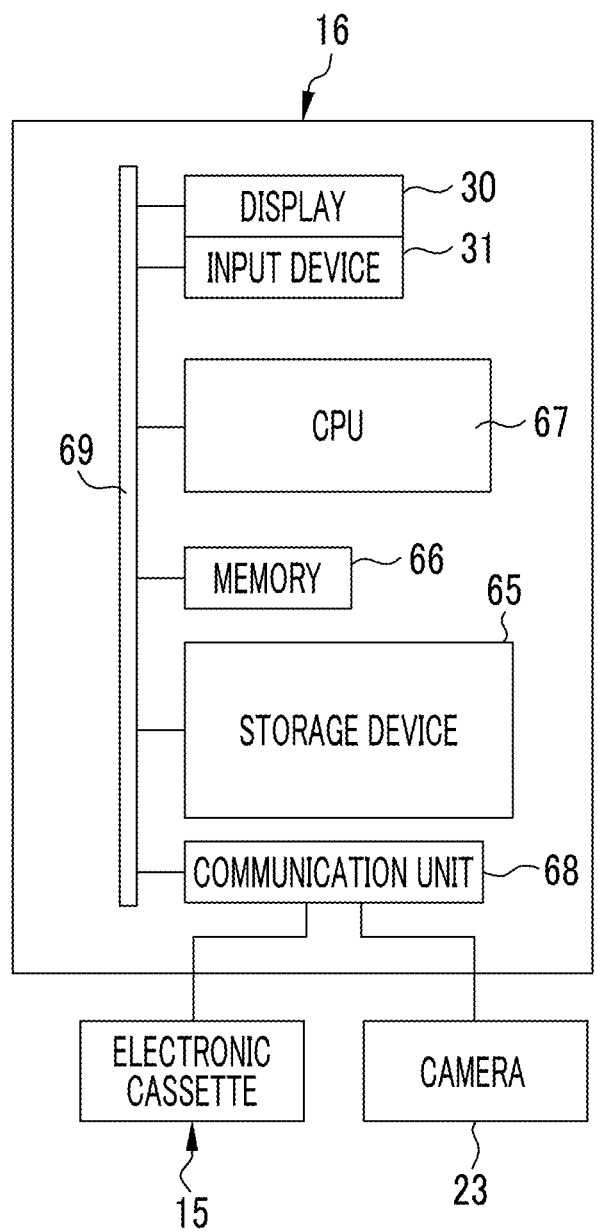
FIG. 7 is a block diagram illustrating a computer forming a console.

In FIG. 7, the console 16 includes a storage device 65, a memory 66, a central processing unit (CPU) 67, and a communication unit 68 in addition to the display 30 and the input device 31. These units are connected to each other through a data bus 69.

The storage device 65 is a hard disk drive or a disk array of a plurality of hard disk drives which is provided in the console 16 or is connected to the console 16 through a cable or a network. For example, the storage device 65 stores a control program, such as an operating system, various application programs, and various kinds of data associated with the programs.

The memory 66 is a work memory that is used by the CPU 67 to perform processes. The CPU 67 loads the program stored in the storage device 65 to the memory 66 and performs the process corresponding to the program to control the overall operation of each unit of the console 16. The communication unit 68 communicates with the electronic cassette 15 and the camera 23 to transmit and receive various kinds of data such as the X-ray image 40 and the camera image 63.

Figure 8:
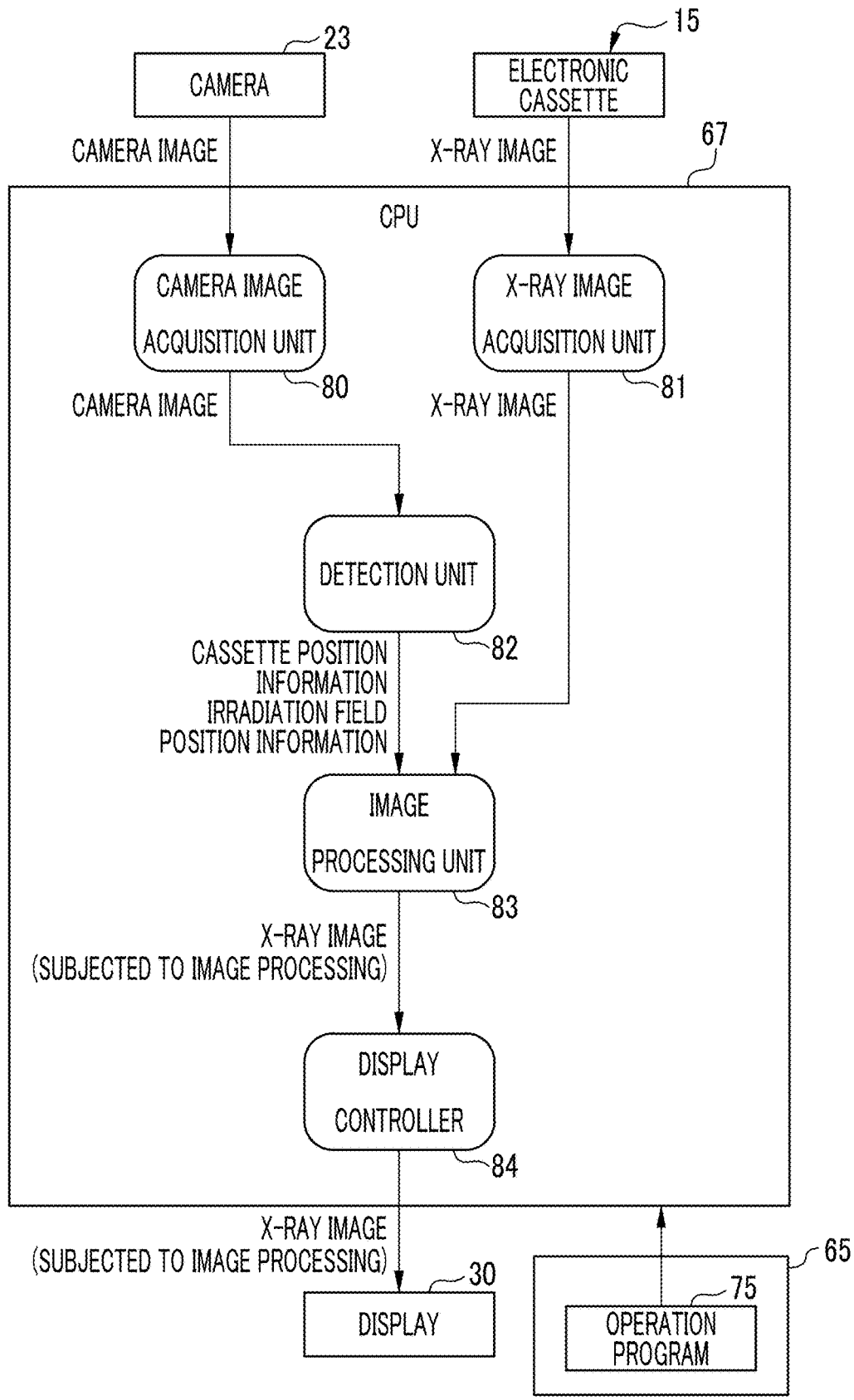
FIG. 8 is a block diagram illustrating a CPU of the console.

In FIG. 8, the storage device 65 stores an operation program 75. The operation program 75 is an application program that causes a computer forming the console 16 to function as an image processing device. In a case in which the operation program 75 is run, the CPU 67 functions as a camera image acquisition unit 80, an X-ray image acquisition unit 81, a detection unit 82, an image processing unit 83, and a display controller 84 in cooperation with, for example, the memory 66.

The camera image acquisition unit 80 has a camera image acquisition function of acquiring the camera image 63 from the camera 23. The camera image acquisition unit 80 outputs the acquired camera image 63 to the detection unit 82. The X-ray image acquisition unit 81 corresponds to a radiographic image acquisition unit and has an X-ray image acquisition function of acquiring the X-ray image 40 from the electronic cassette 15. The X-ray image acquisition unit 81 outputs the acquired X-ray image 40 to the image processing unit 83.

The detection unit 82 has a detection function of detecting the position of the electronic cassette 15 on the basis of the camera image 63. Specifically, the detection unit 82 applies a known image recognition technique, such as pattern matching, to the camera image 63 to recognize the markers 57A to 57C on the front surface 52A of the housing 52 of the electronic cassette 15. Then, the detection unit 82 detects the position coordinates of the recognized markers 57A to 57C in the camera image 63 as the position of the electronic cassette 15. That is, since the markers 57A and 57B are arranged along the imaging region RX, the position of the electronic cassette 15 detected by the detection unit 82 is the position of the imaging region RX. The detection unit 82 outputs the information (hereinafter, referred to as cassette position information) of the detected position of the electronic cassette 15 to the image processing unit 83.

In this example, of course, the marker 57C which is covered by the subject H and is not included in the camera image 63 is not recognized by the detection unit 82. However, in a case in which at least one of the four markers 57A can be recognized, it is possible to detect the position of the electronic cassette 15. Instead of or in addition to the markers 57A to 57C, image recognition may be performed for the contour of the periphery of the front surface 52A.

In addition, the detection unit 82 has a detection function of detecting the position of the irradiation field IF on the basis of the camera image 63. In this embodiment, the irradiation field display light source 22 emits the irradiation field display light LIF and the irradiation field display light LIF is included in the camera image 63 as illustrated in FIG. 6. Therefore, in this embodiment, the detection unit 82 detects the position of the irradiation field IF on the basis of the irradiation field display light LIF. In this case, similarly to the detection of the position of the electronic cassette 15, the detection unit 82 recognizes the contour of the periphery of the region irradiated with the irradiation field display light LIF with a known image recognition technique and detects the position coordinates of the recognized contour in the camera image 63 as the position of the irradiation field IF. At that time, since the irradiation field display light LIF of a special color is emitted, the detection unit 82 recognizes the contour of the periphery of the region irradiated with the irradiation field display light LIF with reference to color information. The detection unit 82 outputs the information (hereinafter, referred to as irradiation field position information) of the detected position of the irradiation field IF to the image processing unit 83.

The image processing unit 83 has an image processing function of performing image processing for the X-ray image 40 from the X-ray image acquisition unit 81 on the basis of the cassette position information and the irradiation field position information from the detection unit 82. The image processing unit 83 outputs the processed X-ray image to the display controller 84.

The display controller 84 performs control such that the processed X-ray image 40 from the image processing unit 83 is displayed on the display 30.

Figure 9:
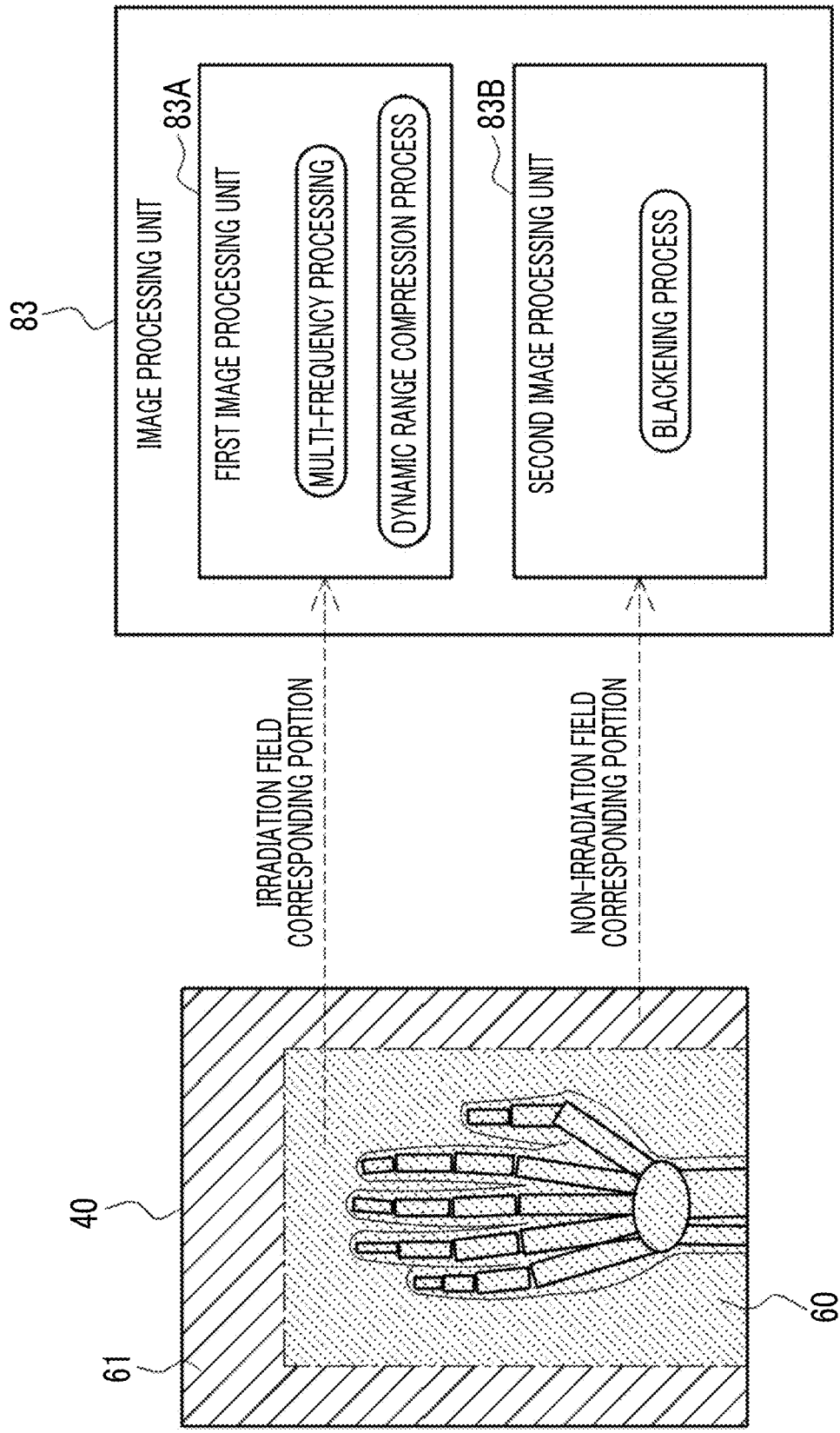
FIG. 9 is a block diagram illustrating an image processing unit.

As illustrated in FIG. 9, the image processing unit 83 includes a first image processing unit 83A and a second image processing unit 83B. The first image processing unit 83A specifies the irradiation field corresponding portion 60 of the X-ray image 40 on the basis of the cassette position information and the irradiation field position information from the detection unit 82. Then, the first image processing unit 83A performs first image processing as the image processing for the irradiation field corresponding portion 60. The second image processing unit 83B specifies the non-irradiation field corresponding portion 61 of the X-ray image 40 and performs second image processing as the image processing for the non-irradiation field corresponding portion 61.

Specifically, the first image processing unit 83A performs multi-frequency processing and a dynamic range compression process as the first image processing for the irradiation field corresponding portion 60. In addition, the second image processing unit 83B performs a blackening process as the second image processing for the non-irradiation field corresponding portion 61.

First, the multi-frequency processing creates a plurality of smoothing images for the X-ray image 40 before the image processing. Then, the multi-frequency processing calculates a difference image between the smoothing images and performs a non-linear conversion process for the difference image. Then, the multi-frequency processing performs frequency enhancement using the sum of the difference images subjected to the non-linear conversion process to enhance the edge of a structure such as a bone. The dynamic range compression process is a portion of the function of the multi-frequency processing. The dynamic range compression process brightens a dark portion of the X-ray image 40, using the sum of the difference images subjected to the non-linear conversion process in the multi-frequency processing, such that the dark portion is easily seen or darkens a bright portion of the X-ray image 40 using the sum of the difference images such that the bright portion is easily seen. The blackening process colors the non-irradiation field corresponding portion 61 black.

Next, the operation of the above-mentioned configuration will be described with reference to the flowcharts illustrated in FIGS. 10 and 11. First, the operator sets a desired imaging menu through the input device 31 of the console 16. Then, a condition setting signal including, for example, the set imaging menu and the irradiation conditions corresponding to the imaging menu is transmitted from the console 16 to the electronic cassette 15. After setting the imaging menu, the operator sets the same irradiation conditions as the irradiation conditions corresponding to the set imaging menu to the radiation source control device 14 through the touch panel 25. Then, the operator starts to relatively position the X-ray source 13, the electronic cassette 15, and the subject H.

For example, in a case in which the image of the hand is captured, the operator places the electronic cassette 15 on the table 17, places the hand of the subject H on the electronic cassette 15, and sets the X-ray source 13 immediately above the subject H, as illustrated in, for example, FIG. 1. In this case, the operator sets the size of the irradiation opening of the irradiation field limiter 21, that is, the irradiation field IF to the radiation source control device 14 through the touch panel 25.

The operator operates the irradiation field display light source 22 such that the irradiation field display light LIF is emitted to the electronic cassette 15. The operator finely adjusts the positions of the X-ray source 13, the electronic cassette 15, and the subject H, using the irradiation field display light LIF, such that a desired positional relationship is obtained.

After completing the positioning, the operator inputs a command to capture the camera image 63 through the input device 31 of the console 16. Then, the imaging command signal to capture the camera image 63 is wirelessly transmitted from the console 16 to the camera 23.

The camera 23 captures the camera image 63 in response to the imaging command signal from the console 16. The camera image 63 is wirelessly transmitted from the camera 23 to the console 16.

Figure 10:
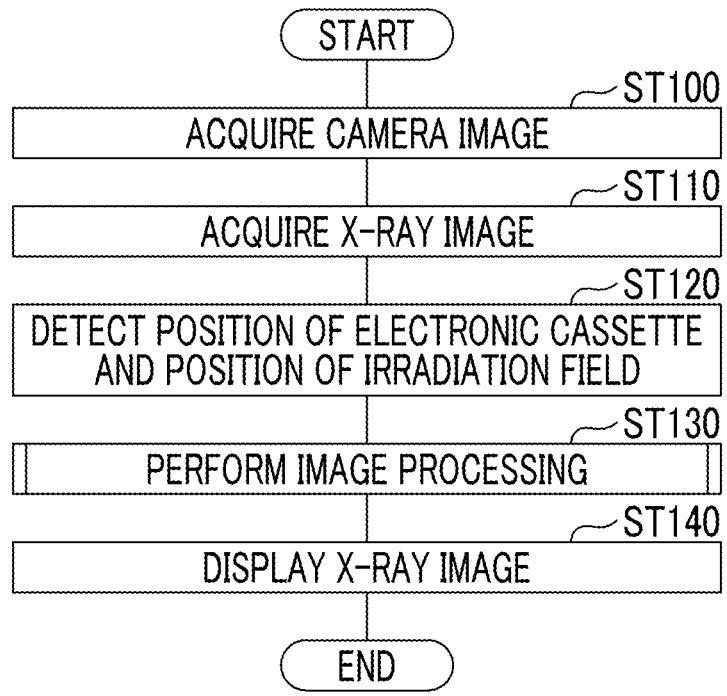
FIG. 10 is a flowchart illustrating the procedure of the process of the CPU of the console.

As illustrated in Step ST100 of FIG. 10, the camera image acquisition unit 80 acquires the camera image 63 from the camera 23 (camera image acquisition step). The camera image 63 is output from the camera image acquisition unit 80 to the detection unit 82.

The operator operates the irradiation switch 28 such that the X-ray source 13 generates X-rays. The front surface 52A of the electronic cassette 15 is irradiated with the X-rays which have been emitted from the X-ray source 13 and then transmitted through the subject H. Then, the electronic cassette 15 detects the X-ray image 40. The X-ray image 40 is wirelessly transmitted from the electronic cassette 15 to the console 16.

As illustrated in Step ST110, the X-ray image acquisition unit 81 acquires the X-ray image 40 from the electronic cassette 15 (corresponding to an X-ray image acquisition step and a radiographic image acquisition step). The X-ray image 40 is output from the X-ray image acquisition unit 81 to the image processing unit 83.

As illustrated in Step ST120, the detection unit 82 detects the position of the electronic cassette 15 and the position of the irradiation field IF on the basis of the camera image 63 from the camera image acquisition unit 80 (detection step). The cassette position information which is the information of the detected position of the electronic cassette 15 and the irradiation field position information which is the positional information of the irradiation field IF is output to the image processing unit 83.

As illustrated in Step ST130, the image processing unit 83 performs image processing for the X-ray image 40 from the X-ray image acquisition unit 81 on the basis of the cassette position information and the irradiation field position information from the detection unit 82 (image processing step).

Figure 11:
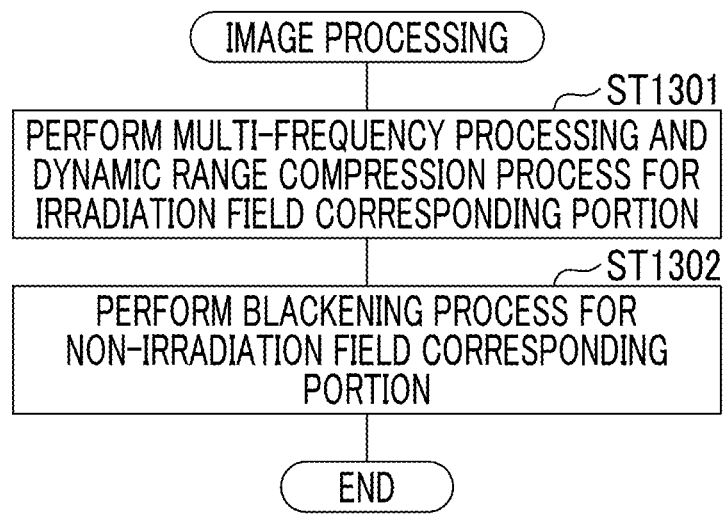
FIG. 11 is a flowchart illustrating the procedure of the process of the image processing unit.
(A) of FIG. 12 illustrates an aspect of free imaging in a case in which an irradiation field is set to be inclined with respect to an imaging region and an arm is an imaging part and (B) of FIG. 12 illustrates an X-ray image.

FIG. 11 illustrates the flow of the image processing step performed by the image processing unit 83. As illustrated in FIG. 9, the first image processing unit 83A performs the multi-frequency processing and the dynamic range compression process as the first image processing for the irradiation field corresponding portion 60 (Step ST1301). Then, the second image processing unit 83B performs the blackening process as the second image processing for the non-irradiation field corresponding portion 61 (Step ST1302). The processed X-ray image 40 subjected to the image processing is output from the image processing unit 83 to the display controller 84. The order of the first image processing in Step ST1301 and the second image processing in Step ST1302 may be reversed.

In Step ST140 of FIG. 10, the display controller 84 displays the processed X-ray image 40 on the display 30. In addition, the console 16 converts the X-ray image 40 into the image file 41 and transmits the image file 41 to the PACS such that the person who requests imaging reads the image file 41.

The console 16 does not analyze the X-ray image 40 to detect the position of the irradiation field IF as in the related art, but detects the position of the irradiation field IF on the basis of the camera image 63 output from the camera 23. Therefore, the position of the irradiation field IF can be detected with higher accuracy than that in detection based on the X-ray image 40 in which the contour of the irradiation field IF is likely to be unclear. Then, it is possible to perform appropriate image processing for the X-ray image 40 on the basis of the information of the detected position of the irradiation field IF.

The effect of the invention will be described in comparison with the related art in which image analysis is performed for the X-ray image 40. As illustrated in (A) of FIG. 12, the following case is considered: the irradiation field IF is set to be inclined with respect to the imaging region RX such that each side of the irradiation field IF is not parallel to each side of the imaging region RX; and the imaging part is an arm including a large number of relatively linear components.

In the image analysis for the X-ray image 40 in the related art, for example, a portion in which pixel values change rapidly is extracted as the boundary between the irradiation field IF and the non-irradiation field NIF. Then, a rectangular region formed at the extracted boundary is detected as the irradiation field. Therefore, in a case in which the irradiation field IF is not rectangular as illustrated in (A) of FIG. 12, it is difficult to detect the position of the irradiation field IF.

Figure 12:
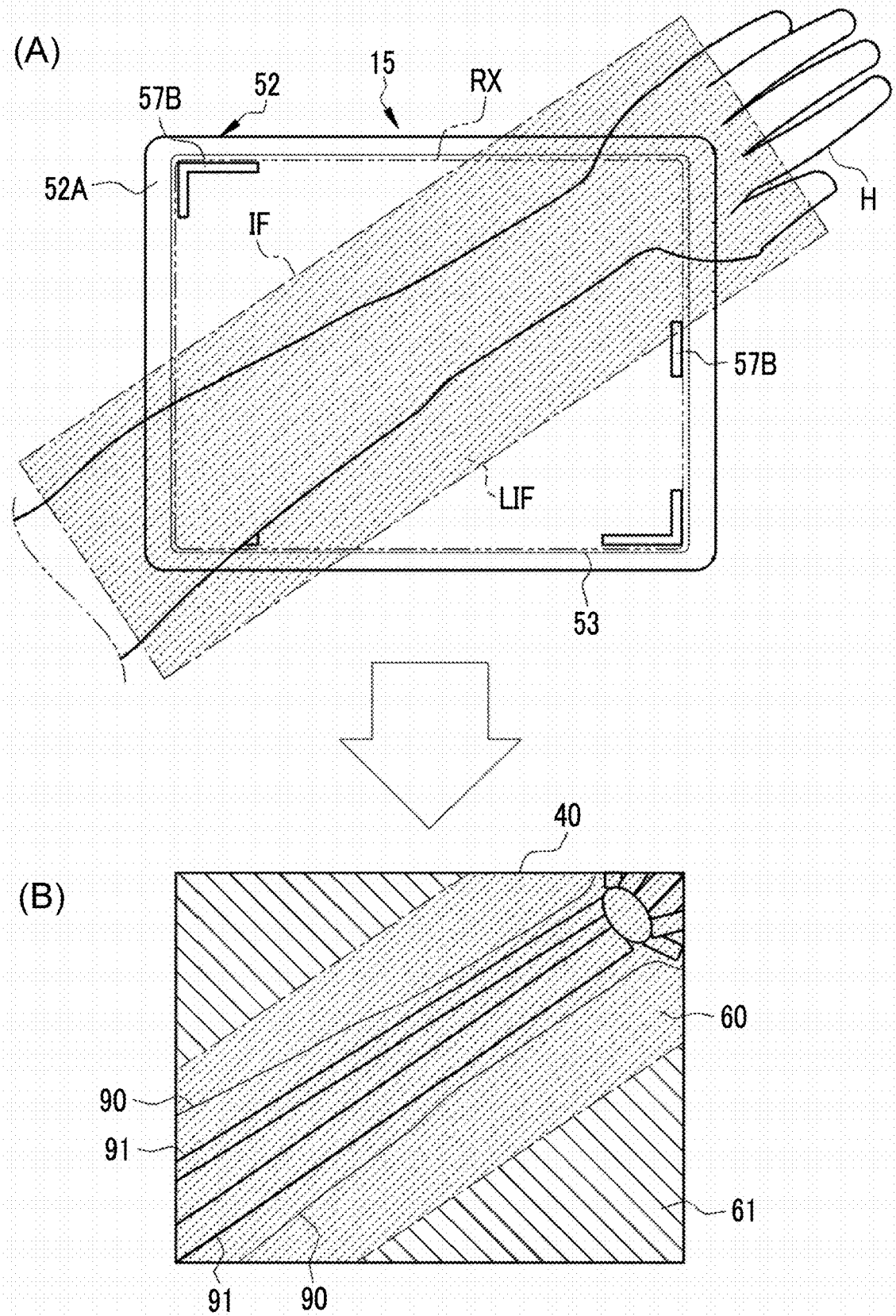

In addition, in a case in which the imaging part is an arm as illustrated in (B) of FIG. 12, the imaging part includes a large number of linear components such as the contour 90 of the arm and the contours 91 of bones (the ulna and the radius). Since the contours 90 and 91 are also the portions in which pixel values change rapidly, the contours 90 and 91 are likely to be falsely extracted as the boundary between the irradiation field IF and the non-irradiation field NIF. In addition, since the contours 90 and 91 are linear, the possibility that the contours 90 and 91 will be falsely extracted as the boundary between the linear irradiation field IF and the linear non-irradiation field NIF increases.

In contrast, in the invention in which the position of the irradiation field IF is detected on the basis of the camera image 63 output from the camera 23, it is possible to detect the position of the irradiation field IF regardless of the X-ray image 40. Therefore, even in a case in which the irradiation field IF is set so as to be inclined with respect to the imaging region RX and the imaging part includes a large number of relatively linear components as illustrated in (A) and (B) of FIG. 12, it is possible to detect the exact position of the irradiation field IF.

That is, since the detection unit 82 detects the position of the irradiation field IF on the basis of the irradiation field display light LIF from the irradiation field display light source 22 included in the camera image 63, it is possible to simply detect the position of the irradiation field IF only by using a known image recognition technique. Since the irradiation field display light source 22 is provided as a standard device in many X-ray sources, it is possible to effectively use the existing devices.

Since the first image processing unit 83A performs the multi-frequency processing and the dynamic range compression process for the irradiation field corresponding portion 60 of the X-ray image 40, it is possible to obtain the X-ray image 40 in which the edge of a structure, such as a bone, is enhanced and the overall contrast is improved and which has quality suitable for diagnosis. In addition, the first image processing is preferably performed only for the irradiation field corresponding portion 60. Therefore, it is possible to reduce the processing load of the first image processing unit 83A.

The second image processing unit 83B performs the blackening process for the non-irradiation field corresponding portion 61. Therefore, it is possible to avoid the situation in which the non-irradiation field corresponding portion 61 is displayed in white and hinders observation.

Figure 13:
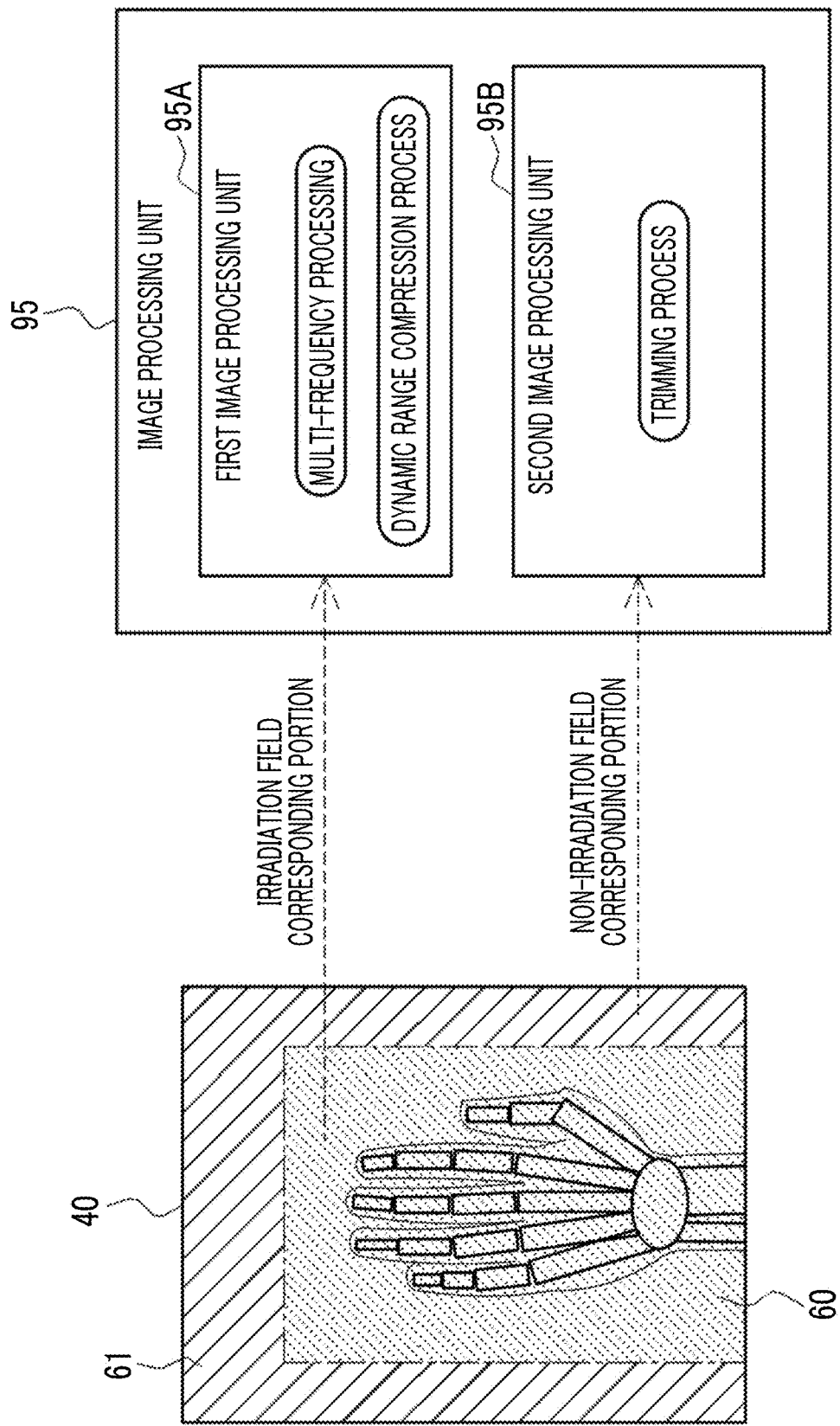
FIG. 13 is a block diagram illustrating another example of the image processing unit.

The second image processing performed for the non-irradiation field corresponding portion 61 is not limited to the blackening process. A second image processing unit 95B of an image processing unit 95 may perform a trimming process which trims the non-irradiation field corresponding portion 61 and leaves only the irradiation field corresponding portion 60 as illustrated in FIG. 13. In this case, similarly to the blackening process, the non-irradiation field corresponding portion 61 is removed. Therefore, it is possible to avoid the situation in which the non-irradiation field corresponding portion 61 is displayed in white and hinders observation.

The first image processing unit 95A has a different reference numeral for convenience, but has the same functions as the first image processing unit 83A.

Second Embodiment

In a second embodiment illustrated in FIGS. 14 and 15, the size (hereinafter, referred to as an in-image size) of the irradiation field IF in the camera image 63 during X-ray imaging is calculated.

Figure 14:
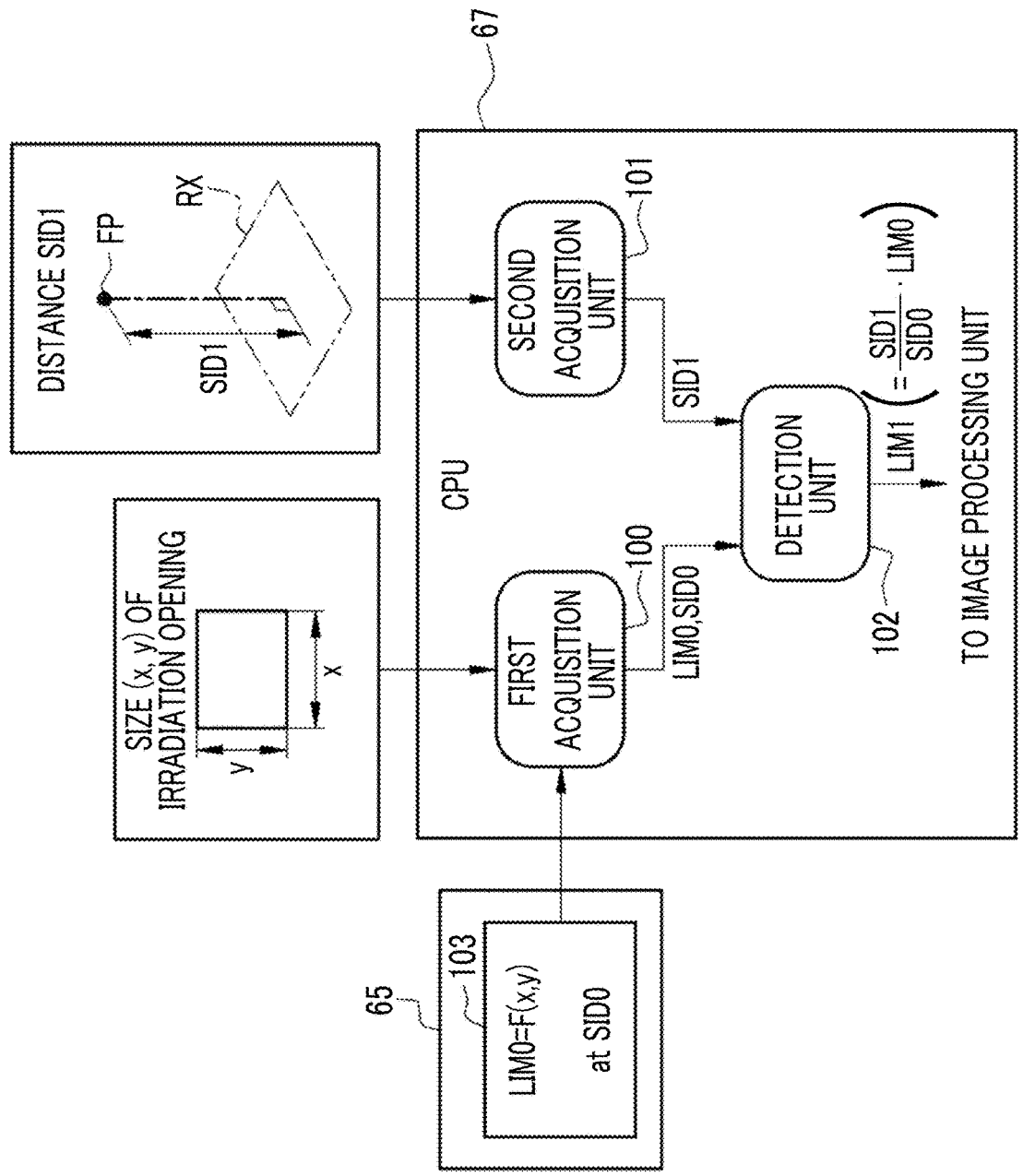
FIG. 14 is a block diagram illustrating a CPU of a console according to a second embodiment.
Figure 15:
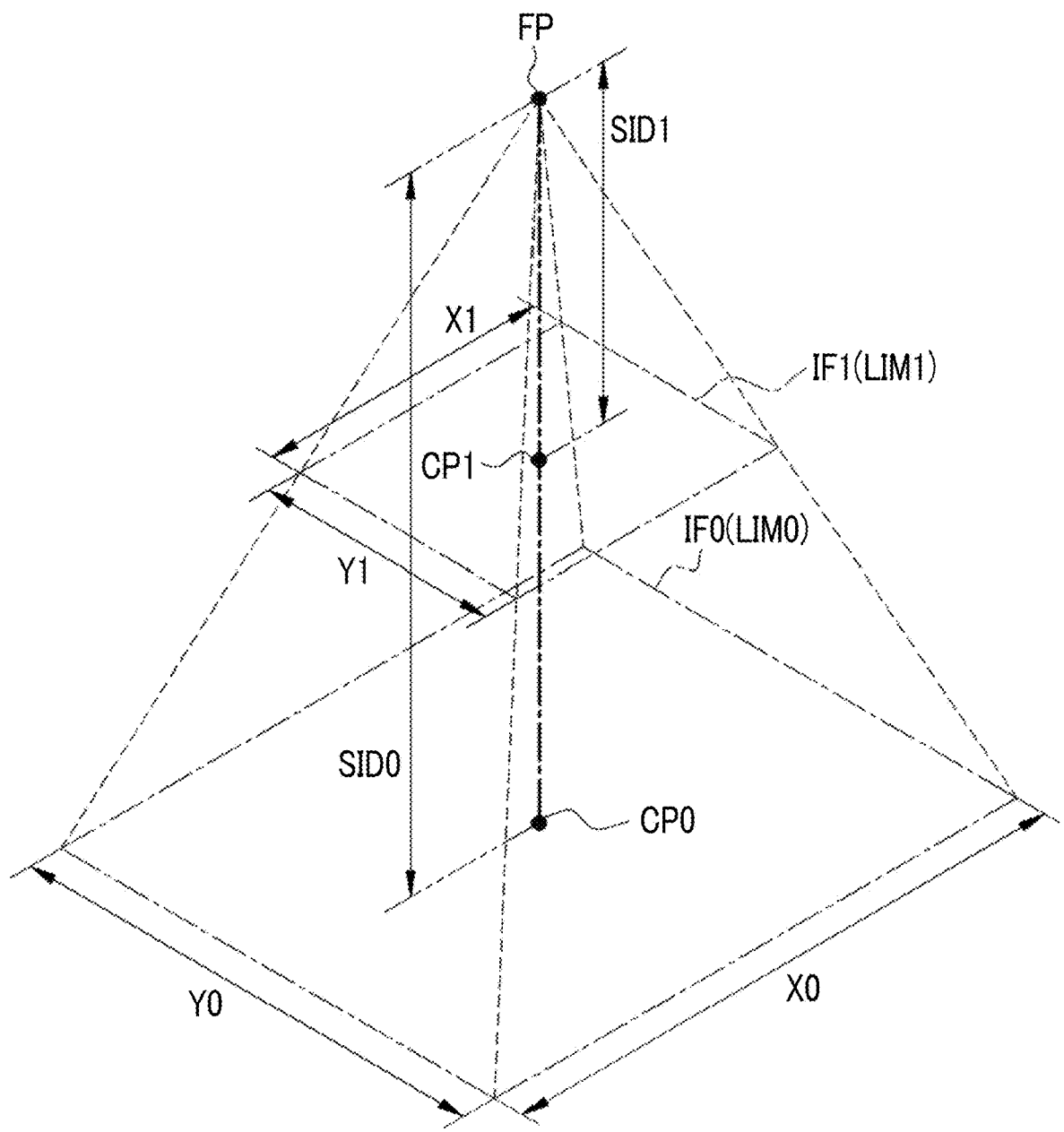
FIG. 15 is a reference diagram illustrating the second embodiment.

In FIG. 14, a CPU 67 of a console 16 according to this embodiment includes a first acquisition unit 100 and a second acquisition unit 101 in addition to the units 80, 81, 83, and 84 (not illustrated in FIG. 14) according to the first embodiment illustrated in FIG. 8. In addition, a detection unit 102 is provided instead of the detection unit 82. Next, the functions of the first acquisition unit 100, the second acquisition unit 101, and the detection unit 102 will be described with reference to FIGS. 14 and 15.

The first acquisition unit 100 acquires the reference size (hereinafter, referred to as a reference in-image size) LIM0 of an irradiation field IF0 in the camera image 63 at a predetermined reference distance SID (source to image receptor distance) 0 from a focal position FP of the X-ray tube 20 of the X-ray source 13 as an end point.

Specifically, first, the first acquisition unit 100 acquires the size (x, y) (the length of the irradiation opening in the vertical and horizontal directions) of the irradiation opening of the irradiation field limiter 21 during X-ray imaging. Then, the first acquisition unit 100 acquires the reference in-image size LIM0 corresponding to the acquired size (x, y) of the irradiation opening on the basis of an arithmetic expression 103 (LIM0=F(x, y)) stored in the storage device 65. The arithmetic expression 103 is a function of the reference in-image size LIM0 having the size (x, y) of the irradiation opening as variables. The first acquisition unit 100 substitutes the acquired size (x, y) of the irradiation opening into the arithmetic expression 103 to acquire the reference in-image size LIM0. The first acquisition unit 100 outputs the acquired reference in-image size LIM0 and the acquired reference distance SID0 to the detection unit 102.

Here, the reference in-image size LIM0 is the lengths X0 and Y0 of the irradiation field IF0, which is projected to a plane having a line connecting the focal position FP and a point CP0 that is the reference distance SID0 away from the focal position FP as a normal line, in the horizontal and vertical directions.

The second acquisition unit 101 acquires a distance SID1 between the focal position FP and the imaging region RX during X-ray imaging. The distance SID1 is the length of a vertical line drawn from the focal position FP to the imaging region RX. The second acquisition unit 101 outputs the acquired distance SID1 to the detection unit 102.

The detection unit 102 calculates an in-image size LIM1 of the irradiation field IF1 in the camera image 63 during X-ray imaging from the reference in-image size LIM0 and the reference distance SID0 from the first acquisition unit 100 and the distance SID1 from the second acquisition unit 101. That is, the in-image size LIM1 is calculated using a homothetic ratio SID1/SID0 illustrated in the following Expression (1):

$$LIM1=(SID1/SID0) \cdot LIM0 \quad (1).$$

Similarly to the reference in-image size LIM0, the in-image size LIM1 is the lengths X1 and Y1 of an irradiation field IF1, which is projected to a plane having a line connecting the focal position FP and a point CP1 that is the distance SID1 away from the focal position FP as a normal line, in the horizontal and vertical directions. Therefore, the above-mentioned Expression (1) is rewritten to the following Expressions (2) and (3):

$$X1=(SID1/SID0) \cdot X0 \quad (2); \text{ and}$$

$$Y1=(SID1/SID0) \cdot Y0 \quad (3).$$

For example, in a case in which the reference distance SID0 is 5 m, X0 is 1 m, Y0 is 50 cm, and the distance SID1 is 2.5 m, the homothetic ratio SID1/SID0 is 2.5/5=0.5. Therefore, X1 is 50 cm and Y1 is 25 cm.

The detection unit 102 converts the calculated in-image size LIM1 into the position coordinates of the contour of the irradiation field IF1 in the camera image 63. Then, the detection unit 102 outputs the converted position coordinates as the irradiation field position information to the image processing unit 83. Since the subsequent processes are the same as those in the first embodiment, the description thereof will not be repeated.

As such, the reference in-image size LIM0 of the irradiation field IF0 in the camera image 63 at the reference distance SID0 and the distance SID1 between the focal position FP and the imaging region RX during X-ray imaging are acquired and the in-image size LIM1 of the irradiation field IF1 in the camera image 63 during X-ray imaging is calculated from the reference in-image size LIM0, the reference distance SID0, and the distance SID1. Therefore, it is possible to detect the position of the irradiation field IF1, without any problem, even in a case in which the irradiation field display light source 22 is out of order and is not capable of emitting the irradiation field display light LIF or a case in which the X-ray source does not include the irradiation field display light source 22.

For example, the operator directly inputs the size (x, y) of the irradiation opening during X-ray imaging to the console 16 through the input device 31. Alternatively, the radiation source control device 14 may transmit the size (x, y) of the irradiation opening during X-ray imaging to the console 16.

Similarly, the operator directly inputs the distance SID1 between the focal position FP and the imaging region RX during X-ray imaging to the console 16 through the input device 31. Alternatively, a distance measurement sensor that measures the distance SID1 may be attached to the X-ray source 13 and the distance measurement sensor may transmit the measured distance SID1 to the console 16. For example, a time-of-flight camera, an ultrasound sensor, or a radar sensor can be used as the distance measurement sensor.

In addition, the distance SID1 may be calculated on the basis of the size of the electronic cassette 15 included in the camera image 63. In this case, the size of the electronic cassette 15 included in the camera image 63 at the reference distance SID0 is stored in the storage device 65 in advance. Then, the distance SID1 is calculated using the homothetic ratio such that the size is equal to the in-image size LIM1 of the irradiation field IF1 in the camera image 63 during X-ray imaging.

The reference in-image size LIM0 corresponding to the size (x, y) of the irradiation opening is calculated by the arithmetic expression 103. However, the invention is not limited thereto. The reference in-image size LIM0 corresponding to the size (x, y) of the irradiation opening may be stored in the storage device 65 in the form of a data table. In this case, the first acquisition unit 100 reads the reference in-image size LIM0 corresponding to the acquired size (x, y) of the irradiation opening from the data table of the storage device 65.

Third Embodiment

In a third embodiment illustrated in FIG. 16, the information of the irradiation field corresponding portion is associated as accessory information 42 of the X-ray image 40 with the X-ray image 40.

In FIG. 16, a CPU 67 of a console 16 according to this embodiment includes an association processing unit 110 in addition to the units 80 to 84 (only the detection unit 82 is illustrated) according to the first embodiment illustrated in FIG. 8.

The detection unit 82 outputs the cassette position information and the irradiation field position information to the association processing unit 110. The association processing unit 110 specifies the irradiation field corresponding portion 60 of the X-ray image 40 on the basis of the cassette position information and the irradiation field position information from the detection unit 82. The association processing unit 110 inserts the information (hereinafter, referred to as irradiation field corresponding portion information) of the specified irradiation field corresponding portion 60 into the accessory information 42 of the image file 41. Specifically, the irradiation field corresponding portion information is the position coordinates of the irradiation field corresponding portion 60 in the X-ray image 40.

As such, since the irradiation field corresponding portion information is associated as the accessory information 42 with the X-ray image 40, an apparatus other than the console 16, for example, a client terminal of the person who requests imaging can perform image processing for the irradiation field corresponding portion 60 with reference to irradiation field corresponding portion information.

In addition, instead of the irradiation field corresponding portion information, non-irradiation field corresponding portion information which is the information of the non-irradiation field corresponding portion 61 may be associated as the accessory information 42 with the X-ray image 40. The detection unit 82 according to the first embodiment is illustrated in FIG. 16. However, the detection unit 102 according to the second embodiment may be used.

The image processing unit may include at least one of the first image processing unit or the second image processing unit.

A motion picture may be captured as the camera image 63 and the position of the electronic cassette 15 and the position of the irradiation field IF may be detected on the basis of the camera image 63 captured immediately before the emission of X-rays starts.

In each of the above-described embodiments, the camera image 63 is used only to detect the position of the electronic cassette 15 and the position of the irradiation field IF. However, in a case in which a motion picture is captured as the camera image 63 and the operator relatively positions the X-ray source 13, the electronic cassette 15, and the subject H, the camera image 63 may be displayed on the display 30 to assist positioning.

In each of the above-described embodiments, for example, the hardware structures of the processing units performing various processes, such as the camera image acquisition unit 80, the X-ray image acquisition unit 81, the detection units 82 and 102, the image processing units 83 and 95 (the first image processing units 83A and 95A and the second image processing units 83B and 95B), the display controller 84, the first acquisition unit 100, the second acquisition unit 101, and the association processing unit 110, are the following various processors.

Various processors include, for example, a CPU, a programmable logic device (PLD), and a dedicated electric circuit. The CPU is a general-purpose processor that executes software (program) to function as various processing units as it is known. The PLD is a processor whose circuit configuration can be changed after it is manufactured, such as a field programmable gate array (FPGA). The dedicated electric circuit is a processor having a dedicated circuit configuration designed to perform a specific process, such as an application specific integrated circuit (ASIC).

One processing unit may be one of the various processors or a combination of two or more processors of the same type or different types (for example, a combination of a plurality of FPGAs and a combination of a CPU and an FPGA). In addition, a plurality of processing units may be formed by one processor. As an example in which a plurality of processing units are formed by one processor, first, one processor is formed by a combination of one or more CPUs and software and the processor functions as the plurality of processing units. Second, a processor which is typified by a system-on-chip (SoC) and in which the overall function of a system including a plurality of processing units is implemented by one IC chip is used. As such, the hardware structure of various processing units is formed by one or more of the various processors.

In addition, specifically, the hardware structure of the various processors is an electric circuit (circuitry) which is a combination of circuit elements such as semiconductor elements.

An image processing device described in the following Supplementary Note 1 can be understood from the above description.

Supplementary Note 1

There is provided an image processing device including 1 a radiographic image acquisition processor that acquires a radiographic image which is based on radiation that has been emitted from a radiation source and transmitted through a subject and is detected by an electronic cassette; a camera image acquisition processor that acquires a camera image output from a camera which is attached to the radiation source and captures an image of at least the electronic cassette; a detection processor that detects a position of the electronic cassette and a position of an irradiation field which is a region irradiated with the radiation on the basis of the camera image; and an image processing processor that performs image processing for the radiographic image on the basis of information of the position of the electronic cassette and information of the position of the irradiation field.

In each of the above-described embodiments, the case in which free imaging is performed using the X-ray imaging system 10 installed in the imaging room has been described as an example. However, the invention can also be applied to a case in which free imaging is performed in a hospital room equipped with a bed for the subject H, using a treatment cart which is a portable X-ray generation apparatus.

The invention is not limited to the X-rays and can also be applied to a case in which other types of radiation including y-rays are used.

The invention is not limited to each of the above-described embodiments and can adopt various configurations without departing from the scope and spirit of the invention. In addition, the invention can be applied to a program and a storage medium storing the program.

EXPLANATION OF REFERENCES

10: X-ray imaging system
11: X-ray generation apparatus
12: X-ray imaging apparatus
13: X-ray source (radiation source)
14: radiation source control device
15: electronic cassette
16: console (image processing device)
20: X-ray tube
21: irradiation field limiter
22: irradiation field display light source
23: camera
25: touch panel
26: voltage generation unit
27: controller
28: irradiation switch
30: display
31: input device
40: X-ray image (radiographic image)
41: image file
42: accessory information
50: sensor panel
51: circuit unit
52: housing
52A: front surface
53: transmission plate
55: scintillator
56: optical detection substrate
57A to 57C: marker
60: irradiation field corresponding portion
61: non-irradiation field corresponding portion
63: camera image
65: storage device
66: memory
67: CPU
68: communication unit
69: data bus
75: operation program
80: camera image acquisition unit
81: X-ray image acquisition unit (radiographic image acquisition unit)
82, 102: detection unit
83, 95: image processing unit
83A, 95A: first image processing unit
83B, 95B: second image processing unit
84: display controller
90: contour of arm
91: contour of bone
100: first acquisition unit
101: second acquisition unit
103: arithmetic expression
110: association processing unit
H: subject
LIF: irradiation field display light FOV: field of view of camera
IF, IF0, IF1: irradiation field
NIF: non-irradiation field
RX: imaging region
ST100 to ST140, ST1301, ST1302: step
FP: focal position of X-ray tube
x, y: size of irradiation opening during X-ray imaging
SID0: reference distance
SID1: distance between focal position and imaging region during X-ray imaging
LIM0: reference in-image size
LIM1: in-image size of irradiation field in camera image during X-ray imaging
CP0, CP1: point
X0, Y0, X1, Y1: lengths of irradiation field in vertical and horizontal directions

What is claimed is:

1. An image processing device comprising:
    a radiographic image acquisition unit that acquires a radiographic image which is based on radiation that has been emitted from a radiation source and transmitted through a subject and is detected by an electronic cassette;
    a camera image acquisition unit that acquires a camera image output from a camera which is attached to the radiation source and captures an image of at least the electronic cassette;
    a detection unit that detects a position of the electronic cassette and a position of an irradiation field which is a region irradiated with the radiation on the basis of the camera image; and
    an image processing unit that performs image processing for the radiographic image on the basis of information of the position of the electronic cassette and information of the position of the irradiation field.

2. The image processing device according to claim 1, wherein the radiation source includes an irradiation field display light source that emits irradiation field display light indicating the irradiation field, and
    the detection unit detects the position of the irradiation field on the basis of the irradiation field display light included in the camera image.

3. The image processing device according to claim 1, wherein the electronic cassette is provided with an imaging region for detecting the radiographic image,
    the image processing device further comprises:
    a first acquisition unit that acquires a reference size LIM0 of the irradiation field in the camera image at a predetermined reference distance SID0 from a focal position of a radiation tube of the radiation source as an end point; and
    a second acquisition unit that acquires a distance SID1 between the focal position and the imaging region during radiography, and
    the detection unit calculates a size LIM1 of the irradiation field in the camera image during, radiography from the reference size LIM0 acquired by the first acquisition unit, the reference distance SID0, and the distance SID1 acquired by the second acquisition unit.

4. The image processing device according to claim 1, wherein the image processing unit includes a first image processing unit that performs first image processing as the image processing for an irradiation field corresponding portion which is a portion of the radiographic image corresponding to the irradiation field or/and a second image processing unit that performs second image processing as the image processing for a non-irradiation field corresponding portion which is a portion of the radiographic image corresponding to a non-irradiation field that is a region which is other than the irradiation field and is not irradiated with the radiation.

5. The image processing device according to claim 3, wherein the radiation source includes an irradiation field limiter having an irradiation opening for setting the irradiation field, and
    the first acquisition unit acquires a size of the irradiation opening during radiography and acquires the reference size LIM0 corresponding to the acquired size of the irradiation opening.

6. The image processing device according to claim 4, wherein the first image processing unit performs, as the first image processing, multi-frequency processing and a dynamic range compression process for the irradiation field corresponding portion.

7. The image processing device according to claim 4, wherein the second image processing unit performs, as the second image processing, a blackening process that colors the non-irradiation field corresponding portion black or a trimming process that trims the non-irradiation field corresponding portion and leaves only the irradiation field corresponding portion.

8. The image processing device according to claim 4, further comprising:
    an association processing unit that associates information of the irradiation field corresponding portion or the non-irradiation field corresponding portion as accessory information of the radiographic image with the radiographic image.

9. A method for operating an image processing device comprising:
    a radiographic image acquisition step of acquiring a radiographic image which is based on radiation that has been emitted from a radiation source and transmitted through a subject and is detected by an electronic cassette;
    a camera image acquisition step of acquiring a camera image output from a camera which is attached to the radiation source and captures an image of at least the electronic cassette;
    a detection step of detecting a position of the electronic cassette and a position of an irradiation field which is a region irradiated with the radiation on the basis of the camera image; and
    an image processing step of performing image processing for the radiographic image on the basis of information of the position of the electronic cassette and information of the position of the irradiation field.

* * * * *